US007917297B2

(12) United States Patent
Cherepinsky et al.

(10) Patent No.: US 7,917,297 B2
(45) Date of Patent: Mar. 29, 2011

(54) METHODS, SOFTWARE ARRANGEMENTS, STORAGE MEDIA, AND SYSTEMS FOR GENOTYPING OR HAPLOTYPING POLYMORPHIC GENETIC LOCI OR STRAIN IDENTIFICATION

(75) Inventors: Vera Cherepinsky, Sandy Hook, CT (US); Bhubaneswar Mishra, Great Neck, NY (US)

(73) Assignee: New York University, New York, NY (US)

( * ) Notice: Subject to any disclaimer, the term of this patent is extended or adjusted under 35 U.S.C. 154(b) by 1232 days.

(21) Appl. No.: 10/567,126

(22) PCT Filed: Aug. 2, 2004

(86) PCT No.: PCT/US2004/024766
§ 371 (c)(1),
(2), (4) Date: Aug. 15, 2006

(87) PCT Pub. No.: WO2005/013091
PCT Pub. Date: Feb. 10, 2005

(65) Prior Publication Data
US 2007/0043514 A1 Feb. 22, 2007

Related U.S. Application Data

(60) Provisional application No. 60/492,210, filed on Aug. 1, 2003.

(51) Int. Cl.
*G01N 33/48* (2006.01)
(52) U.S. Cl. ........................................ 702/19
(58) Field of Classification Search ...................... 702/19
See application file for complete search history.

(56) References Cited

U.S. PATENT DOCUMENTS
6,582,909 B1 6/2003 Bougueleret et al.

FOREIGN PATENT DOCUMENTS
WO WO8910977 11/1989

OTHER PUBLICATIONS

Cutler et al. "High-Throughput Variation Detection and Genotyping Using Microarrays," Genome Research (2001) vol. 11, pp. 1913-1925.*
H.J. Noreen et al., "Validation of DNA-based HLA-A and HLA-B testing of volunteering for a bone marrow registry through parallel testing with serology", Tissue Antigens, 2001:57; pp. 221-229.
Andreas Krause et al., "Accurate method for fast design of diagnostic oligonucleotide probe sets for DNA microarray", Second IEEE International Workshop on High Performance Computational Biology, 2003 pp. 1-9.
Haiyuan Yu et al. "Chromosomal location effects on gene expression: unraveling the contributions from chromatin super-structure and microarray artifacts", Department of Molecular Biophysics and Biochemistry Yale University , 2004.
Yuval Kluger et al., "Relationship between gene co-expression and probe localization on microarray slides", Department of Molecular Biophysics and Biochemistry Yale University , 2004.
Jiang Qian et al., "Spatial artifacts in microarray data: spurious correlations and the techniques to remove them", Department of Molecular Biophysics and Biochemistry Yale University , 2004.
Sam Rash et al., "String barcoding: Uncovering Optimal Virus Signatures", Proceedings of the Sixth Annual International Conference on Computational Biology, 2002 pp. 254-261.
David J. Lockhart, "Expression monitoring by hybridization to high-density oligonucleotide arrays", Nature Biotechnology, Dec. 1996, vol. 14, p. 1675-1680.
Vera Cherepinsky et al., "HLA Typing", Courant Institute of Mathematical Science, New York University, Jul. 30, 2003, pp. 1-14.
Fugen Li et al., "Selection of optimal DNA oligos for gene expression arrays", 2001, vol. 17 No. 11, pp. 1067-1076.
Clarissa Consolandi et al., "Detection of HLA Polymorphisms by Ligase Detection Reaction and a Universal Array Format: A Pilot Study for Low Resolution Genotyping" Elsevier 2003, vol. 64, pp. 168-178.
Lars Kaderali et al., "An Algorithm to Select Target Specific Probes for DNA Chips", 2001 http://citeseer.nj.nec.com/kaderali01algorithm.html pp. 1-10.
James Boreman et al., "Probe selection algorithms with applications in the analysis of microbial communities", Bioinformatics 2001, vol. 17, pp. S39-S48.
Michael Luby, "A Simple Parallel Algorithm for the Maximal Independent Set Problem", ACM, 1985 pp. 1-10.
K. Cao et al., "Reviews in Immunogenetics", vol. 1 No. 2, 1999.
Thomas M. Cover et al., "Elements of Information Theory" John Wiley and Sons, New York 1991.

* cited by examiner

*Primary Examiner* — Jerry Lin
(74) *Attorney, Agent, or Firm* — Dorsey & Whitney LLP

(57) ABSTRACT

The present invention relates generally to systems, methods, storage media, and software arrangements for genotyping and/or haplotyping a sequence of polymorphic genetic loci in a deoxyribonucleic acid (DNA) sample or identifying a strain variant from the DNA sample. Exemplary embodiments of systems, methods, storage media, and software arrangements may perform the optimization of the design of one or more microarrays, each containing a set of oligonucleotide probes capable of detecting one or more known genotypes and/or haplotypes at given polymorphic genetic loci or identifying the strain variant, by optimizing the set of oligonucleotides to be incorporated into the microarrays and by optimizing the arrangement of a set of oligonucleotides on the microarrays. The optimization may be achieved through the application of one or more optimization procedures. The instant invention may be useful in typing individuals at the HLA loci or other polymorphic genetic loci, or may be employed to quickly identify viral or bacterial pathogens from which genome sequence information is available.

50 Claims, 4 Drawing Sheets

METHODS, SOFTWARE ARRANGEMENTS, STORAGE MEDIA, AND SYSTEMS FOR GENOTYPING OR HAPLOTYPING POLYMORPHIC GENETIC LOCI OR STRAIN IDENTIFICATION

CROSS-REFERENCE TO RELATED APPLICATIONS

This application is a national stage application of PCT Application No. PCT/US2004/024766 which was filed on Aug. 1, 2004 and published in English on Feb. 10, 2005 as International Publication No. WO 2005/013091 (the "International Application"), This application also claims priority from U.S. Patent Application Ser. No. 60/492,210, filed on Aug. 1, 2003 (the "'210 Application"). The entire disclosures of these applications are incorporated herein by reference. This application claims priority from the International Application pursuant to 35 U.S.C. §365, and from the '210 Application pursuant to 35 U.S.C. §§119(e) and 365.

FIELD OF THE INVENTION

The present invention relates generally to systems, methods, and software arrangements for genotyping or haplotyping polymorphic genetic loci or strain identification.

BACKGROUND OF THE INVENTION

The human leukocyte antigen ("HLA") region on chromosome 6 is highly polymorphic. In particular, the sequence of this region varies from person to person. See, e.g., Consolandi et al., *Human Immunology* 2003, 64:168. Approximately 1,750 different sequence variants or "alleles" have been identified to date at the HLA locus. There are many biological implications of the high degree of heterogeneity of this region. For example, the presence or absence of a given HLA allele or "HLA type" may predict the presence or absence of diseases, dictate the course of treatment for a patient, or, most notably, determine the compatibility of a potential transplant recipient with the donor organ or bone marrow.

One of the approaches to finding the right allele is to design a microarray experiment that provides the allele as an answer. In fact, HLA typing by sequence hybridization with sequence-specific oligonucleotide probes ("SSOP") is currently practiced by the National Marrow Donor Program ("NMDP") for donor-recipient matching, along with more traditional serological-based methods. See, e.g., Cao et al., *Reviews in Immunogenetics* 1999, 1:177; and Noreen et al., *Tissue Antigens* 2001, 57:221. In a format that is popular in many current test methods, the DNA samples to be classified are amplified with locus-specific primers, and spotted onto the microarray chips, thus resulting in multiple copies of identical chips; each chip is then hybridized to a different probe. See Balazs et al., *Human Immunology* 2001, 62:850; Consolandi et al., *Human Immunology* 2003, 64:168. This methodology necessitates a new design process every time a new set of patient samples must be classified. Moreover, most of the currently used techniques are both time-consuming and lack optimality.

The system, process, storage medium and software arrangement according to one exemplary embodiment of present application provides a graph model on the set of potential probes in which the HLA typing problem is formulated mathematically as an optimization problem. According to the present application, it is also possible to utilize an algorithm for solving the optimization problem. The processes of translating the typing problem to the graph model and translating the optimizing probe set back to an experimental design for HLA typing are also described. Extensions of the graph model to more detailed physical models are discussed as well.

SUMMARY OF THE INVENTION

Embodiments of systems, processes, storage media and software arrangements for genotyping or haplotyping the polymorphic genetic loci or strain identification according to the present invention may optimize the design of one or more microarrays, each containing a set of oligonucleotides that are capable of detecting known genotypes or haplotypes at given polymorphic genetic loci. This can be done by optimizing the set of oligonucleotides to be incorporated into the microarrays and/or by optimizing the arrangement of a set of oligonucleotides on the microarrays. Such optimization may also be achieved through the application of one or more optimization algorithms. The present invention may be useful in typing individuals at the HLA loci or other polymorphic genetic loci, and/or may be employed to quickly identify viral or bacterial pathogens from which genome sequence information is available.

In contrast to the conventional systems and methods according to the present invention, the sequence-specific probes may be placed on a microarray chip, and each patient sample can be applied to the chip to allow the hybridization with one or more of the chip-bound probes to occur. With an appropriate selection of probes, the same chip can be used for all classifications. However, the number of probes to be used, their sequence compositions, and their arrangement on the chip are some of the design variables that should preferably be considered in preparing the microarray. A general solution to solving these design problems is preferably one that allows the "recognition" of all existing alleles at a target locus, and/or that can decide that the given DNA sequence contains an allele that is not in the "known" list. Such an allele may be a new, previously unknown allele, or one of the very rare alleles that occur so infrequently that they are not considered HLA types. For example, an exemplary embodiment of the present invention is directed toward systems, processes, storage media and software arrangements for genotyping or haplotyping a DNA sample at one or more polymorphic loci contained in the sample through the use of microarray μA, which can be defined by a set of oligonucleotide hybridization probes configured on the surface of the microarray in a two-dimensional arrangement. The process of querying a given polymorphic locus in a DNA sample (hereafter referred to as a "target" sequence) by a hybridization experiment can be denoted by the expression $$(T_j, \mu A_k) \rightarrow D \rightarrow \hat{T}_j \qquad (1)$$

where $T_j$ is the true allele contained in the target sequence, $\mu A_k$ is the microarray used in the query, D is the data output of the hybridization experiment, and $\hat{T}_j$ is the allele inferred from the data. Both processes in equation (1) are described below.

The problem of genotyping or haplotyping then can be formulated as that of designing, e.g., the "best" microarray, namely, the set and arrangement of oligonucleotide probes that "works" for all known alleles (i.e., $\forall j$). In the notation employed herein, this means finding $\mu A_k$ which solves the optimization $$\min_{\text{type } j} \sum w_j E[\Pi_{T_j \neq \hat{T}_j}] \Leftrightarrow \min_{\text{type } j} \sum w_j Pr(T_j \neq \hat{T}_j). \quad (2)$$

Here, $\Pi_X$ is the indicator function $$\Pi_X = \begin{Bmatrix} 1, & \text{if } X \text{ is true} \\ 0, & \text{otherwise} \end{Bmatrix}$$

and $w_j$ is the weight assigned to type j. Initially, $w_j$ can be set such that $w_j=1 \forall j$. At a later point it may be desirable to weigh different HLA types differently, based on the frequency of their occurrence in human population or some other criteria.

According to another exemplary embodiment of the present invention, a pseudocode can be provided to select an optimal set of oligonucleotide probes to be incorporated into the one or more microarray devices to be used to genotype or haplotype polymorphic loci or identify the strain present in a DNA sample. According to this exemplary embodiment, vertex boosting weights (initially set to probe information weights) can be used to define a probability distribution on a vertex set present in a graphical representation of "response vectors" derived from each potential probe sequence. On each iteration of a boosting loop, a random subset of a specified size can be selected according to the current probability distribution. All edges in the induced subgraph on this random subset are broken, with one of the terminal vertices removed. The boosting weights of the elements of the subset can then be modified so that the vertices that stayed in the subset are more likely, and the vertices that were thrown out are less likely to be chosen on the next iteration. The boosting loop may be terminated after a predetermined number of iterations have been performed without further improvement to the list of top independent sets. In addition, the boosting loop can be restarted several times with original probe information weights, which prevents convergence to a local optimum.

The exemplary embodiments of the systems, processes, storage media and software arrangements of the present invention are generally more beneficial in comparison to conventional methods in that they require fewer probes, thereby minimizing the cost associated with the use of such probes. The exemplary embodiments of the systems, processes, storage media and software arrangements of the present invention are also preferable to conventional methods in that they can minimize competition among neighboring probes, thereby reducing or eliminating the occurrence of systematic biases in the error process.

For a better understanding of the present invention, together with other and further objects, reference is made to the following description, taken in conjunction with the accompanying drawings, and its scope will be pointed out in the appended claims.

DETAILED DESCRIPTION OF THE DRAWINGS

For a more complete understanding of the present invention and its advantages, reference is now made to the following description, taken in conjunction with the accompanying drawings, in which.

DETAILED DESCRIPTION OF THE INVENTION

An exemplary embodiment of the present invention is directed to systems, processes, storage media and software arrangements for genotyping or haplotyping polymorphic genetic loci (e.g., an HLA locus, in a subject) or strain identification. HLA haplotyping or genotyping may assist in, e.g., a prediction of a presence or absence of diseases, selecting a course of treatment for a patient, and/or determining the compatibility of a potential transplant recipient with the donor organ or bone marrow. The systems, processes, storage media and software arrangements of the present invention also may be useful for e.g., identifying the presence of an unknown pathogen, including but not limited to a virus or a bacterium, in a sample.

By providing a relatively rapid, inexpensive, and potentially highly accurate way of genotyping or haplotyping polymorphic genetic loci or strain identification, the exemplary systems, processes, storage media and software arrangements of the present invention also can be useful in elucidating genotype/phenotype correlations in complex genetic disorders, i.e., those in which more than one gene may play a significant role, or in genetic diseases characterized by the presence of a relatively large number of genotypes or haplotypes at polymorphic loci. The knowledge obtained from the exemplary systems, processes, storage media, and software arrangements of the present invention therefore may assist in facilitating the diagnosis, treatment, and prognosis of individuals bearing a given phenotype.

Figure 1A:
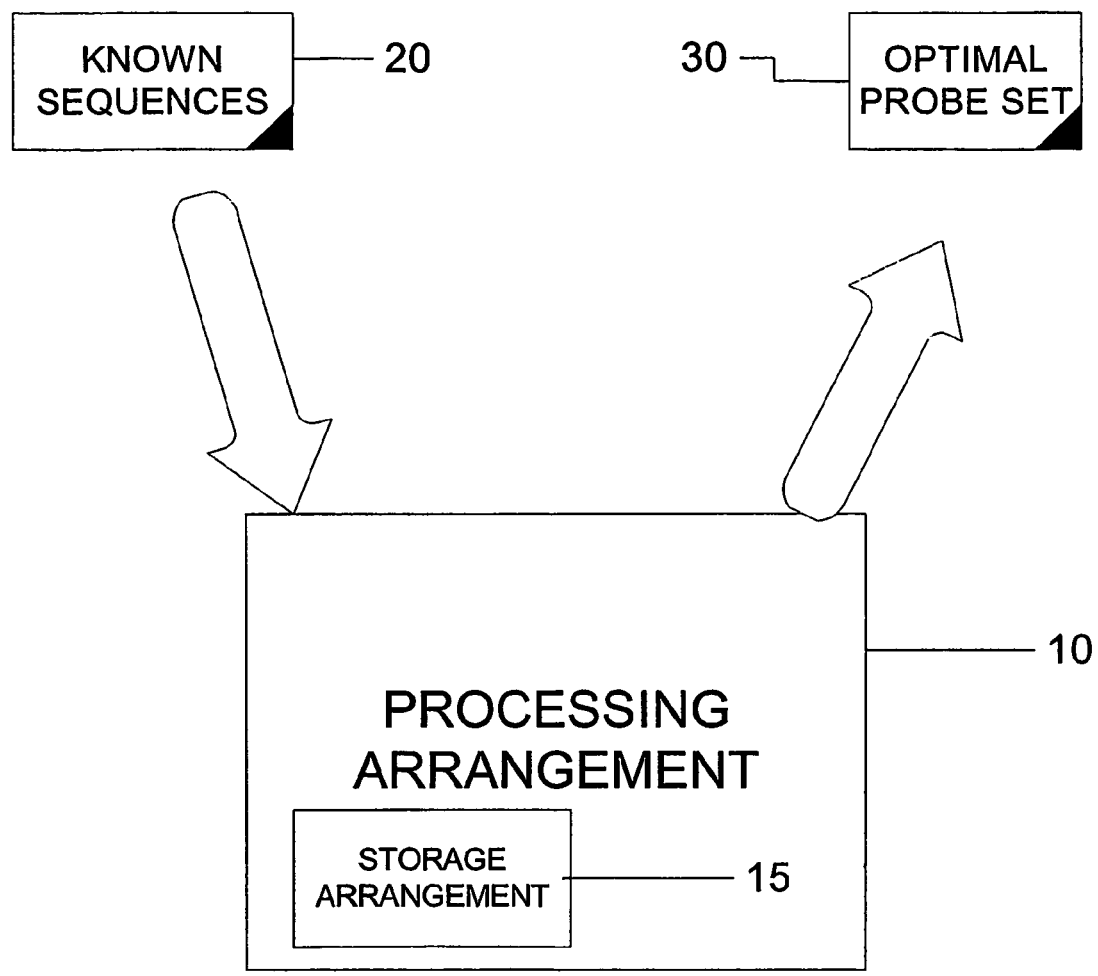
FIG. 1A is an exemplary embodiment of a system according to the present invention for determining an optimal set of oligonucleotide probes for use in a microarray designed to perform genotyping or haplotyping of polymorphic genetic loci.

FIG. 1A shows an exemplary embodiment of a system according to the present invention for determining a particular set of oligonucleotide probes for a use in a microarray designed to perform genotyping and/or haplotyping of at least one polymorphic genetic locus. For example, the system includes a processing arrangement 10 (e.g., a computer), which stores a computer program on a storage arrangement 15 (e.g., memory, hard drive, etc.) to execute the exemplary techniques described herein below. In particular, the computer program, when executed by the processing arrangement 10, causes the processing arrangement to obtain known sequences representing classes, e.g., HLA allele sequences, from an external source 20 or any source (as described below). Then the processing arrangement 10 applies a probe selection technique according to the present invention. Thereafter, the processing arrangement 10 outputs the results of the execution of this technique.

Figure 1B:
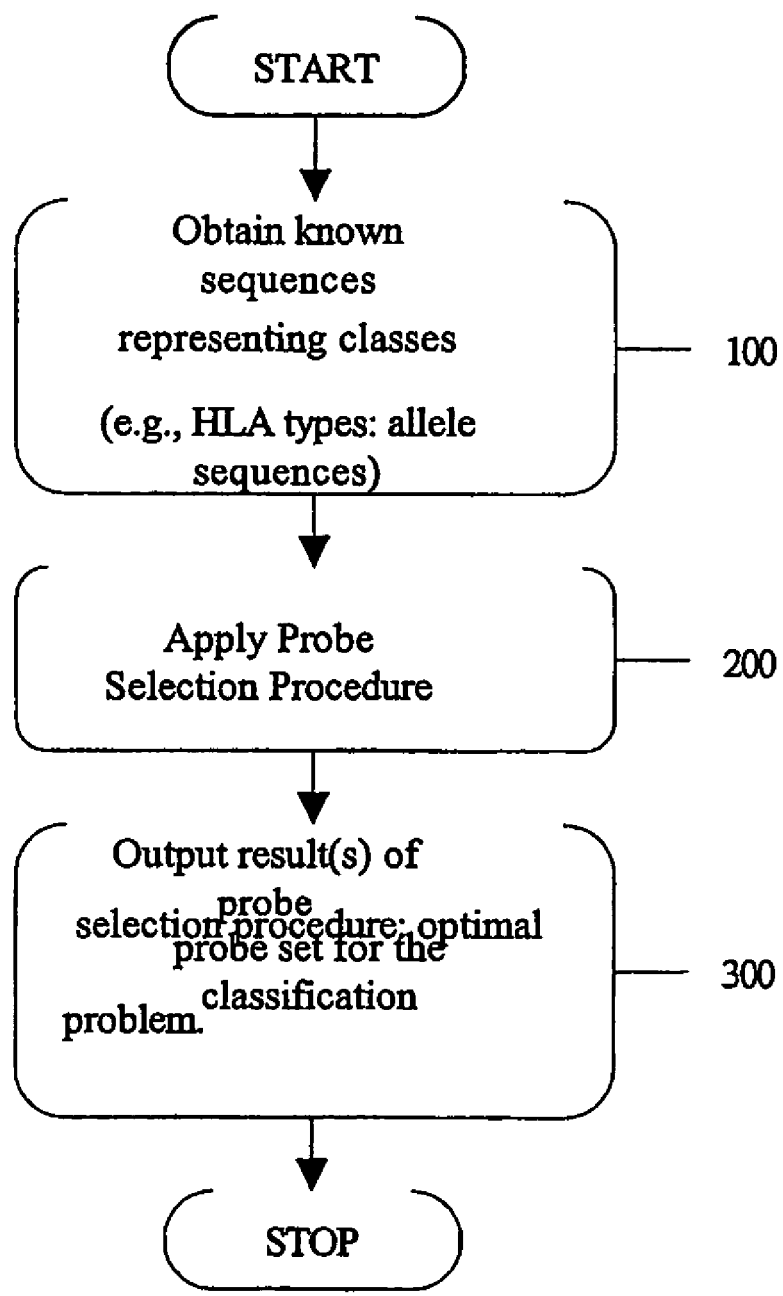
FIG. 1B is an exemplary embodiment of a procedure according to the present invention for determining an optimal set of oligonucleotide probes for use in a microarray designed to perform genotyping or haplotyping of polymorphic genetic loci.

FIG. 1B illustrates a first exemplary embodiment of a process for determining an optimal set of oligonucleotide probes for use in a microarray designed to perform genotyping or haplotyping of polymorphic genetic loci or strain identification which can use the exemplary system shown in FIG. 1A. In this exemplary embodiment, the process executes a first step 100 in which nucleotide sequences of known genotypes or haplotypes at predetermined polymorphic loci, or strain-specific sequences, may be obtained. Such information can be obtained from a number of sources. For example, this data can be obtained from genetic databases including, but not limited to, GenBank and/or other databases maintained by public or private (commercial and noncommercial) institutions. The databases suitable for use with the systems, processes, storage media and software arrangements of the present invention will be readily apparent to those of ordinary skill in the art of DNA sequencing. Alternatively, such information may-be obtained from the prior direct, sequencing of one or more test samples.

Once a set of known sequences corresponding to genotypes or haplotypes at polymorphic genetic loci or strains is assembled, the probe selection procedure 200 of the present invention may be applied to this set to identify an optimal subset of oligonucleotide probes required to genotype or haplotype the polymorphic genetic loci or identify the strain. This can be executed by the processing arrangement of FIG. 1A. The optimization of the set of oligonucleotide probes may include, but is not limited to, the determination of the overall lengths of the various probes, their sequence compositions, and the minimum number of probes required to identify all selected target genotypes or haplotypes or strains. Many if not all selected target genotypes or haplotypes or strains may include all known genotypes or haplotypes at predetermined polymorphic genetic loci or strains, or a subset thereof. For example, the identification may be limited only to those alleles that are most prevalent in the population from which the DNA sample to be genotyped and/or haplotyped has been obtained.

In another step of the process for determining the optimal set of oligonucleotide probes of FIG. 1B, an optimal subset of oligonucleotide probes preferred for genotyping and/or haplotyping polymorphic genetic loci or strain identification may be generated by the probe selection technique 200 and processing arrangement 10. The optimal probe set 300 may then be arranged on one or more microarray devices to determine the genotype or haplotype of polymorphic genetic loci or identify the strain present in a DNA sample.

Another exemplary embodiment of the present invention further relates to the optimal arrangement of the optimal set of oligonucleotide probes on the one or more microarray devices. The exemplary arrangement of the probes may be based on one or more "conceptual" measures of probe distance. The "conceptual" probe distance can use available biological knowledge about the portions of the genome containing the probes in question, as well as a measure of competition between these probes, as described in Chapter 3 of Cherepinsky, *Ph.D. Thesis*, New York University 2003. An exemplary recursive technique according to the present invention can facilitate a separation between the "nearest" probe pairs by at least a specified minimum physical distance on the chip. This optimized arrangement can be designed to be disruptive to neighborhoods, defined with respect to the "conceptual" probe distance. Thus, the exemplary arrangement can place conceptually nearby probes far apart on the surface, thereby minimizing the likelihood for competitive interactions between neighboring probes.

Figure 2:
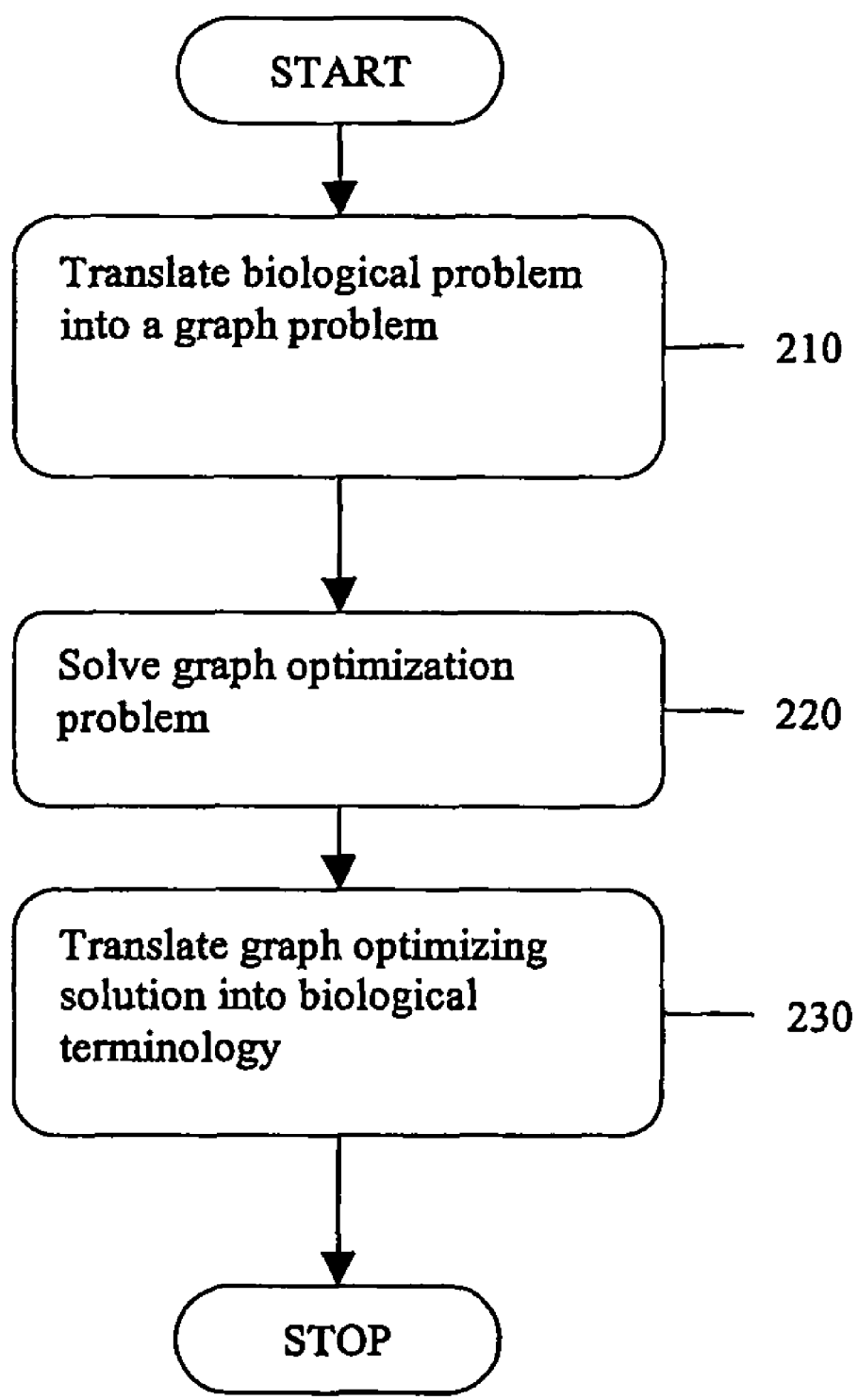
FIG. 2 is a first exemplary embodiment of a probe selection procedure (Shown in FIG. 1B) of the present invention for determining an optimal set of oligonucleotide probes for use in a microarray designed to perform genotyping or haplotyping of polymorphic genetic loci.

FIG. 2 illustrates a first exemplary embodiment of the probe selection algorithm 200 of the present invention for determining the optimal set of oligonucleotide probes. In this exemplary embodiment, the biological problem to be solved, e.g., designing an optimal set of probes to be used on a microarray for determining the genotype or haplotype of polymorphic genetic loci, such as the human HLA region, or strain, variation may first be translated into a graph optimization problem 210. The graph optimization problem can then be solved (item 220) through an application of the exemplary technique according to the present invention. The graph optimization solution 230 can then be translated back into the context of the biological problem to be solved.

Figure 3:
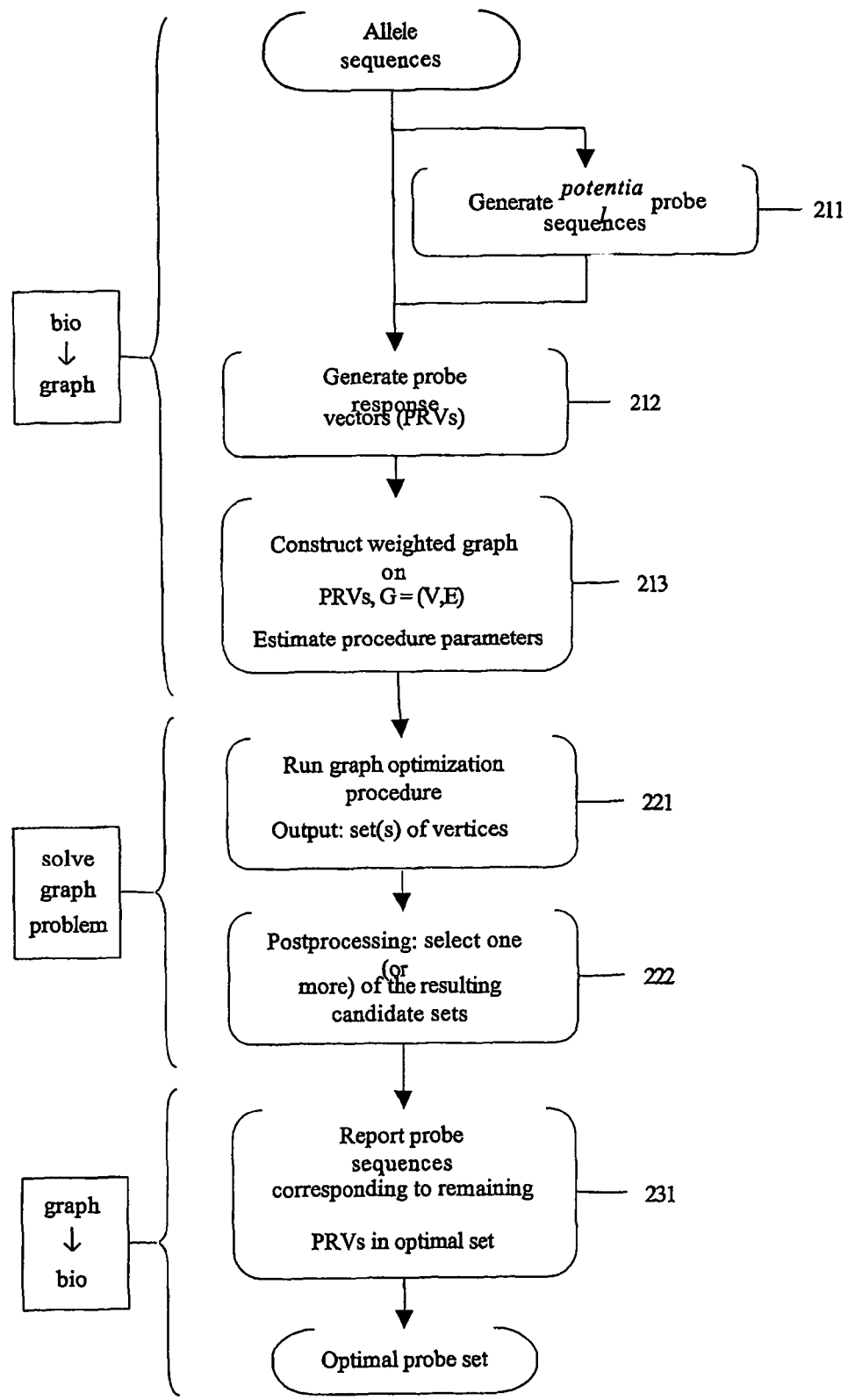
FIG. 3 is a second exemplary embodiment of the probe selection procedure shown in FIG. 1B of the present invention for determining an optimal set of oligonucleotide probes for use in a microarray designed to perform genotyping or haplotyping of polymorphic genetic loci, in which exemplary embodiments of certain steps of FIG. 2 are further illustrated.

FIG. 3 shows a second exemplary embodiment of the probe selection technique (see process 200 of FIG. 1B) according to the present invention for determining the optimal set of oligonucleotide probes, in which the exemplary embodiments of the processes 210 and 220 of FIG. 2 are further illustrated. In this exemplary embodiment, selected target genotypes and/or haplotypes, which may include all known genotypes or haplotypes at one or more predetermined polymorphic genetic loci or a subset thereof, depending on whether pre-processing has been performed, may be used to generate potential probe sequences 211. The potential probe sequences 211 can then be used to generate probe response vectors (PRVs) 212. Using the PRVs 212, a complete edge-weighted and vertex-weighted graph G=(V,E) 213 may be constructed and the algorithm parameters estimated and set. Said parameters include the following: M, the upper bound on the size of the independent set sought; a, the scaling factor used to modify boosting weights of vertices on each iteration of the algorithm; ρ, the edge threshold; parameters minRestartNum and noImprovements, used to set loop termination conditions; as well as unnamed parameters such as the size of the "current-best" list of independent sets. Criteria for estimating M are obtained via probabilistic analysis, discussed in section C.6 of present application. Other parameters are chosen by trial and error.

Once the graph G is constructed, the exemplary technique of the present invention may be applied to identify one or more optimal subsets of PRVs (step 221), which are output from this exemplary technique. In a post-processing procedure, one or more of the candidate optimal subsets 222 can be selected for a maximum discriminatory power by testing allele coding vectors for redundancy.

The PRVs present in the optimal subset may then be converted back into probe nucleotide sequences by reporting the DNA sequence associated with the probe used to generate each PRV contained in the optimal-subset (item 231). This exemplary procedure may be equivalent to translating the solution of the graph optimization problem back into a biological context.

Overall Process Description According to the Present Invention

A. Mathematical Formulation

1. Definitions

Let the different HLA types, or alleles, be denoted by $T_j$, j=1, . . . , N. (Here, N=1750, the approximate number of known HLA types.) Let a given microarray be denoted by $\mu A_k$, k ∈ ℕ, where a microarray is defined by a set of hybridization probes and their two-dimensional arrangement on the chip surface. The process of querying the given DNA sequence (hereafter referred to as a "target" sequence) by hybridization can be denoted by the expression $$(T_j, \mu A_k) \to D \to \hat{T}_j \qquad (1)$$

where $\hat{T}_j$ is the true allele contained in the target sequence, $\mu A_k$ is the microarray used in the query, D is the data output of the hybridization experiment, and $\hat{T}_j$ is the allele inferred from the data. Both processes in (1) are described below.

The problem of HLA typing can then be formulated as that of designing the best microarray, namely, the set and arrangement of probes, which "works" for all known HLA types (i.e., ∀j). In the present notation, this can mean finding μA$_k$ which solves the optimization problem $$\min \sum_{type\ j} w_j E[\Pi_{T_j \neq \hat{T}_j}] \Leftrightarrow \min \sum_{type\ j} w_j Pr(T_j \neq \hat{T}_j). \quad (2)$$

Here, $\Pi_X$ is the indicator function $$\Pi_X = \begin{Bmatrix} 1, & \text{if } X \text{ is true} \\ 0, & \text{otherwise} \end{Bmatrix}$$

and $w_j$ is the weight assigned to type j. Initially, $w_j$ can be set such that $w_j=1\ \forall j$. At a later point, it may be desirable to weigh different HLA types differently, based on the frequency of their occurrence in human population or some other criteria.

There are several procedures that should be considered in detail: obtaining data D from an experiment based on allele $T_j$ and microarray μA$_k$ (described below in Section A.2), inferring allele $\hat{T}_j$ from the data (described below in Section A.3), generating potential microarrays for the typing experiments (described below in Section A.4), and selecting the optimal microarray (Section B).

2. $(T_j, \mu A_k) \rightarrow D$

Consider the set of probes $\{P_{1,k}, \ldots, P_{n(k),k}\}$ constituting microarray μA$_k$, initially neglecting their arrangement. Ideally, the outcome of the hybridization of the target sequence with each probe P would be binary: 1, if the target contains a subsequence complementary to P, and 0, otherwise. Using n=n(k) probes then yields a binary string of length n, or, alternately, a vector of length n, as a code for the target sequence. In practice, hybridization results may not necessarily be binary. In particular, the measurements are the analog intensity values corresponding to the amount of formed probe-target complex for each probe. In addition, in an attempt to "factor out" the non-specific signal, each probe can often be present in two versions: one (e.g., a perfect match, or "pm") perfectly complementary to a region on the target, and the other (e.g., a mismatch, or "mm") slightly mismatched, the latter usually containing a single base mismatch near the center of the probe. This is the case, for example, in Affymetrix GeneChips. In such setup, the signal from probe P may be the match-to-mismatch ratio, i.e., the ratio of the intensities corresponding to the matched and mismatched probe-target complexes. Furthermore, the signal can be log-transformed, so that the hybridization outcome for probe P is really the value of $$\log\left(\frac{TP_{pm}}{TP_{mm}}\right)$$

The situation may further be complicated because the probes may hybridize to positions on the target other than those they were designed to detect—this is known as "cross-hybridization." In addition, the fact that many probes are present in the system may cause the signal (i.e., the hybridization outcome) from a given probe to differ from the signal of the same probe in the absence of other probes. This is described in more detail in Cherepinsky, *Ph.D. Thesis*, New York University 2003, Chapter 3.

Thus, the actual result of a hybridization experiment is a vector of n measurements, $D \in \mathbb{R}^n$.

3. $D \rightarrow \hat{T}_j$

To infer the allele from the n-vector, the ideal process should be referred to again, where the outcome is $D \in \{0,1\}^n$. If the probes are selected in such a way so as to provide a distinct binary string for each known allele (so that the Hamming distance $d_H$ between any pair of data vectors $D_i$, $D_k$ is at least 1), then these n probes can be sufficient to identify the allele of the target sequence. What is preferred is to query the sequence with the n probes and read off the allele to which the pattern corresponds. Furthermore, if it is required that $d_H(D_i, D_k) \geq \alpha$ for some $\alpha > 1$, then the discrimination power can be increased and error-correction is possible. This is discussed in greater detail below (e.g., Section B.6).

In a practical setting, $D \in \mathbb{R}^n$. Thus, as a first procedure, some thresholding process must be applied to D to reduce it to a binary string.

4. Generating Potential Microarrays a. Selection of Informative Probes. A set of n probes, each of length L, that are at least d letters apart (pairwise), must be provided for optimal discrimination among the allele sequences.

If L is not specified, it can be chosen arbitrarily (say, 20), or allowed to vary from probe to probe.

With no restrictions, a very large n can be chosen; for example, every possible 20-mer could be used as a probe. However, this would result in $4^{20}=2^{40}=(2^{10})^4>(10^3)^4=10^{12}$, or over a trillion, probes. Such a large set may not be desirable, since many of these probes would give the same results, and it is too expensive to produce all of them. Allowing both n and L to vary may give an even larger number of potential probe sequences.

The probe design problem relates to selecting which of the probes are most useful in discriminating among the given allele sequences, and how many (or rather, how few) one can use appropriately.

b. Arrangement of Probes on the Chip. When a set of probes has been selected using techniques described herein above, a question still remains of how to arrange these probes on the microarray chip. Several studies indicate that the patterns observed in the results of chip experiments may be due to the arrangement of probes on the chip. See e.g., Kluger et al., submitted to *Nature Genetics*, 2004 at URL http://bioinfo.mbb.yale.edu/~kluger/pipeline/KLUGERetal_NG.pdf; Yu et al., submitted to *Nature Biotechnology*, 2004 at URL http://bioinfo.mbb.yale.edu/~kluger/pipeline/YQK_NB.pdf; and Qian et al., submitted to *Biotechniques*, 2004 at URL http://bioinfo.mbb.yale.edu/~kluger/pipeline/QYK_artifact.pdf. In particular, it has been observed that the probes are arranged on a chip based on the labels of the genes they represent, and a gene label is often related to the function and/or disorder in which the gene is involved. As a result, genes of shared function have similar labels and are coexpressed, generating monochromatic bands on microarray chip scans.

These studies indicate that additional consideration should be given to the arrangement of the probes on the chip, based on certain "conceptual" measure of probe distance. The "conceptual" probe distance can use available biological knowledge about the portions of the genome containing the probes in question, as well as a measure of competition between these probes, as discussed Chapter 3 of Cherepinsky, *Ph.D. Thesis*, New York University 2003. The recursive technique described below can ensure that the "nearest" probe pairs would be separated by at least a specified minimum physical distance on the chip. It is designed to be disruptive to neighborhoods, defined with respect to the "conceptual" probe distance. Thus, the exemplary technique places conceptually nearby probes far apart on the surface.

Consider a bijective function $f: \{0, \ldots, N^2-1\} \to \{0,\ldots,N-1\} \times \{0,\ldots,N-1\}$ that maps every pair of "nearby" points in the domain space to a pair of "distant" points in the range space. In particular, the following devised function $f$ with the following property should be considered: For every $x, y$, if $|x-y| \leq 4^\alpha$, then $\|f(x)-f(y)\|_1 \geq N/(2^{\alpha+1})$. This function likely gives an optimal placement. If the elements of the domain space satisfy other distance properties, this technique can be suitably generalized to handle similar properties with respect to the new distance metric.

This function can play an important role in determining how to place a set of oligonucleotide probes on a microarray surface in such a manner that if two probes are close to one another in their genome locations then they are reasonably far apart on the array. Thus, a placement determined by the function can minimize the competition among the probes for the genomic targets, as well as the systematic biases in the error processes.

Inductively, a uniform family of functions $f_k$ may be defined as follows. Let $k < \lg N$.

$$f_{k+1}: \{0, \ldots, N^2-1\} \to \{0, \ldots, N-1\} \times \{0, \ldots, N-1\}$$
$$: x \mapsto \langle i, j \rangle.$$

$f_{k+1}$ is defined in terms of $f_k$, $$f_k: \{0, \ldots, N^2/4-1\} \to$$

$$\{0, \ldots, N/2-1\} \times \{0, \ldots, N/2-1\},$$

as follows:

$$f_{k+1}(x) = \begin{cases} f_k(\lfloor \frac{x}{4} \rfloor), & \text{if } x \equiv 0 \bmod 4 \\ f_k(\lfloor \frac{x}{4} \rfloor) + \langle 0, \frac{N}{2} \rangle, & \text{if } x \equiv 1 \bmod 4 \\ f_k(\lfloor \frac{x}{4} \rfloor) + \langle \frac{N}{2}, 0 \rangle, & \text{if } x \equiv 2 \bmod 4 \\ f_k(\lfloor \frac{x}{4} \rfloor) + \langle \frac{N}{2}, \frac{N}{2} \rangle, & \text{if } x \equiv 3 \bmod 4 \end{cases} \quad (3)$$

This function can be generalized, without its general properties being affected, by including a random permutation $\pi_{k+1}: \{0, \ldots, 3\} \to \{0, \ldots, 3\}$ as follows:

$$f_{k+1}(x) = \begin{cases} f_k(\lfloor \frac{x}{4} \rfloor), & \text{if } x \equiv \pi_{k+1}(0) \bmod 4 \\ f_k(\lfloor \frac{x}{4} \rfloor) + \langle 0, \frac{N}{2} \rangle, & \text{if } x \equiv \pi_{k+1}(1) \bmod 4 \\ f_k(\lfloor \frac{x}{4} \rfloor) + \langle \frac{N}{2}, \frac{N}{2} \rangle, & \text{if } x \equiv \pi_{k+1}(2) \bmod 4 \\ f_k(\lfloor \frac{x}{4} \rfloor) + \langle \frac{N}{2}, \frac{N}{2} \rangle, & \text{if } x \equiv \pi_{k+1}(3) \bmod 4 \end{cases}$$

Herein below, $k$ may take the value $(\lg N-1)$, and the base case is given by the function $$f_2: \{0, \ldots, 15\} \to \{0, \ldots, 3\} \times \{0, \ldots, 3\}$$

where
$$0 \mapsto \langle 0,0 \rangle\, 1 \mapsto \langle 0,2 \rangle\, 2 \mapsto \langle 2,0 \rangle\, 3 \mapsto \langle 2,2 \rangle\, 4 \mapsto \langle 0,1 \rangle$$
$$5 \mapsto \langle 0,3 \rangle\, 6 \mapsto \langle 2,1 \rangle\, 7 \mapsto \langle 2,3 \rangle\, 8 \mapsto \langle 1,0 \rangle\, 9 \mapsto \langle 1,2 \rangle$$
$$10 \mapsto \langle 3,0 \rangle\, 11 \mapsto \langle 3,2 \rangle\, 12 \mapsto \langle 1,1 \rangle\, 13 \mapsto \langle 1,3 \rangle$$
$$14 \mapsto \langle 3,1 \rangle\, 15 \mapsto \langle 3,3 \rangle \quad (4)$$

This base map can be described in matrix format as follows:

$$\begin{bmatrix} 0 & 4 & 1 & 5 \\ 8 & 12 & 9 & 13 \\ 2 & 6 & 3 & 7 \\ 10 & 14 & 11 & 15 \end{bmatrix} \quad (5)$$

Taking $N=2^l$, $N^2=4^l$ probes can be placed by applying $f_l: \{0, \ldots, 4^l-1\}$, which after $l-2$ recursive steps, defined in equation (3), may reduce to the base case $f_2: \{0, \ldots, 15\}$ shown in equations (4) and (5).

Function $f_l$ can have the following distance properties. Let $D(i, j)$ be the distance between probes $p_i$ and $p_j$, when arrayed on a line (by relabeling the probes, one can view this as the index separation $|i-j|$). Let $d(i, j)$ be their distance when arrayed on the surface. Then, the mapping $f_l$ may guarantee that for all $p_i, p_j$ for which $D(i, j) \leq 4^k$, $d(i, j) \geq 2^{l-k-1}$, where $k=0, \ldots, l-1$. Furthermore, if $d(i, j)=1$, that is $p_i$ is placed next to $p_j$ on the surface, then $D(i, j) \geq 3 \cdot 4^{l-2}$.

For example, let $l=3$. There are $N^2=4^l=64$ probes, which are placed by $f_3$ according to $$\begin{bmatrix} 0 & 16 & 4 & 20 & 1 & 17 & 5 & 21 \\ 32 & 48 & 36 & 52 & 33 & 49 & 37 & 53 \\ 8 & 24 & 12 & 28 & 9 & 25 & 13 & 29 \\ 40 & 56 & 44 & 60 & 41 & 57 & 45 & 61 \\ 2 & 18 & 6 & 22 & 3 & 19 & 7 & 23 \\ 34 & 50 & 38 & 54 & 35 & 51 & 39 & 55 \\ 10 & 26 & 14 & 30 & 11 & 27 & 15 & 31 \\ 42 & 58 & 46 & 62 & 43 & 59 & 47 & 63 \end{bmatrix}$$

The probe distances

| k | D | d |
|---|---|---|
| 0 | 1 | 4 |
| 1 | 4 | 2 |
| 2 | 16 | 1 | likely satisfy the condition that if $D \leq 4^k$, then $d \geq N/2^{k+1} = 2^{l-k-1}$.

The problem of an automatic generation of probe sets for DNA microarrays is described in Krause et al., *Second IEEE International Workshop on High Performance Computational Biology* (HiCOMB 2003), online proceedings at URL http://hpc.eece.unm.edu/HiCOMB/proceedings.html. However, the work described by Krause et al. aims for a probe set that is, even in ideal circumstances, asymptotically much larger than the one generated by the exemplary embodiments of the present invention.

Other biological problems, such as identifying an unknown pathogen as a member of a list of known pathogens, be they viral (see Rash and Gusfield, in *Proceedings of the Sixth Annual International Conference on Computational Biology* (RECOMB '02), ACM Press, pp. 254-261) or bacterial (see Borneman et al., *Bioinformatics* 2001, 17:S39), likely have the same mathematical formulation as the problem of HLA typing discussed here. Those applications can also benefit from the improvements to existing approaches provided by the exemplary embodiments of the present invention.

B. Definitions

The exemplary problem of selecting the optimal microarray is described below. The problem of selecting the constituent probes can be reduced to a "best independent set" problem. The following sections can define the graph model employed, as well as the meaning of the term "best independent set," and describe the optimizing algorithm.

1. Notation

There are N known alleles, and n potential probes. Each probe can be described by a "response vector" $\vec{v}_j \in \{0,1\}^N$, $j=1,\ldots,n$. The response vector data can be represented in tabular form:

|        | $\vec{v}_1$ | $\vec{v}_2$ | $\cdots$ | $\vec{v}_n$ |
|--------|------|------|------|------|
| $HLA_1$ | 1 | 0 | $\cdots$ | 1 |
| $HLA_2$ | 1 | 1 | $\cdots$ | 0 |
| $\vdots$ | $\vdots$ | $\vdots$ |  | $\vdots$ |
| $HLA_N$ | 0 | 0 | $\cdots$ | 1 |

(6)

Column j is the response vector for probe $\vec{v}_j$:

$$\vec{v}_j = (v_j[1], v_j[2], \ldots, v_j[N])^T, \quad (7)$$

and row i is the code for allele i, which we will call $HLA_i$:

$$HLA_i = (v_1[i], v_2[i], \ldots, v_n[i]) \quad (8)$$

2. Original Graph

Each potential probe can form a vertex in the graph. Conceptually, an edge in the graph should connect two probes with shared characteristics.

First, essentially a complete edge- and vertex-weighted undirected graph G=(V,E) on n vertices is constructed, where n is the number of potential probes. In a general problem formulation, n can be very large. For each probe length L, there are likely $4^L$ possible probes. For instance, as shown in above in Section A.4, there may be over a trillion possible probes of length 20. Thus, the graph in the probe interaction model can be very large.

Second, weights are assigned to each vertex v and to each edge e, $0 \leq w(v)$, $w(e) \leq 1$. The weight of a vertex can be initially set to the "information content" of the corresponding probe response vector (PRV) with respect to the HLA typing problem:

$$w(v) = \min\{\text{percentage of 0's, percentage of 1's}\}/100. \quad (9)$$

The term "information content" can be used here differently than defined in information theory, where it may mean the minimum amount of information needed to send a string. See e.g., Cover and Thomas. *Elements of Information Theory*. John Wiley and Sons, New York. 1991. Ideally, if possible, all vertices should have weight 0.5. A vertex with a weight too close to zero can be uninformative, and the corresponding probe should only be used if it serves to differentiate an allele that is not distinguishable by using other, more informative probes.

The weight of an edge is initially set to the scaled Hamming distance of the probe response vectors represented by its endpoints:

$$w(e) = \text{Hamming distance/vector length} \quad (10)$$

with values close to zero corresponding to sequence-similar probes.

3. Thresholded Graph

Third, the graph G is transformed by thresholding the edges. A threshold $\rho$, is selected and used to generate a modified graph $G_{mod} = (V, E_{mod})$, where $$E_{mod} = \{e \in E: w(e) \leq \rho\}$$

is a set of unweighted edges, and the set of weighted vertices V is unchanged. The choice of threshold $\rho$ will be discussed in further detail below in section D. Hereafter, this modified vertex-weighted graph is employed and denoted by G.

An independent set can be defined on the graph. An independent set is defined as a set of vertices such that for any pair of vertices, there is no edge between them. See Dictionary of Algorithms and Data Structures at NIST at URL http://www.nist.gov/dads/. In particular, a set of vertices V' ⊂ V can be an independent set if (u ∈ V' and v ∈ V') implies that $\{u, v\} \notin E$.

4. Exemplary Goal

The best microarray can be defined above in Section A. The corresponding concept is now formulated on the graph model. The best independent set can be defined as a maximum weight yet minimum size independent set. Thus, such a set S ⊂ V must be an independent set, have maximum weight $w(S) = \Sigma_{v \in S} w(v)$, and minimum cardinality |S|. The condition of independence is meant to preclude any unintended interaction among the chosen probes. Maximum weight provides S with maximum discrimination power. Minimum size likely ensures that the smallest collection of probes is used to perform the preferred functions.

Since all vertex weights are nonnegative, the requirements of maximum weight and minimum cardinality are clearly contradictory. The definition can be relaxed somewhat by specifying a priori the desired size M of the set, and looking instead for the maximum weight independent set of size $\leq M$.

C. Optimization Procedure

To achieve this goal, a modification of a Maximal Independent Set procedure, described in Luby, *Proceedings of the Seventh Annual ACM Symposium on Theory of Computing* (*STOC* '85), pp. 1-10, is utilized.

1. Procedure Pseudocode

Given graph G and set size M:

a) Initialization:
  (i) Initialize a "current-best" list of independent sets, with associated information weights. It stores a list of the best, say, 20, independent sets seen so far, sorted by information weight.

b) Restart Loop: Execute at least minRestartNum times; if the "current-best list" is not full (i.e., does not have 20 independent sets) by then, keep repeating until the list is filled.
  (i) Initialize boosting weights; this was accomplished by setting the boosting weights to the information weights of the vertices:

$$\forall v \in V, w_b(v) \leftarrow w(v).$$

(ii) Boosting Loop: Repeat until no improvements have been made to the "current-best" list for a fixed number of iterations (say, five iterations).
    aa. Choose a set S of M vertices randomly from V, with $$P(v \in S) = \frac{w_b(v)}{\sum_{u \in V} w_b(u)}.$$

bb. For each edge {u,v} in G|$_S$ (the induced subgraph on S), eliminate one of the endpoint vertices. This leaves a set, $S_1$, of K≦M independent vertices.

cc. Adjust the boosting weights of vertices in S; for example, increase the boosting weights of the vertices in $S_1$:

$w_b(v) \leftarrow a\, w_b(v)\ \forall v \in S_1$ and decrease the boosting weights of the vertices in S-$S_1$:

$$w_b(v) \leftarrow \frac{1}{a} w_b(v) \quad \forall\, v \in S - S_1$$

where a≧1 is some previously selected constant.

dd. If $S_1$ is not already in the "current-best" list and provides an improvement over some current member of the list, reset the noImprovements counter, locate an appropriate location for $S_1$ in the list, and update the list. Otherwise, make a note that no changes to "current-best" list were made on this iteration (ie., increment the noImprovements counter).

(iii) If the condition for continuing the restart loop holds (namely, minRestartNum restarts have not yet been executed or the "current-best" list is not yet full), reset the noImprovements counter and repeat step (b).

2. Procedure Description

The procedure can utilize vertex boosting weights (e.g., initially set to probe information weights) to define a probability distribution on the vertex set. On each iteration of the boosting loop (step b.ii above), a random subset of a specified size can be selected according to the current probability distribution (step b.ii.aa). All edges in the induced subgraph on this random subset may be broken, with one of the terminal vertices removed (step b.ii.bb). The boosting weights of the elements of the subset can then be modified (step b.ii.cc), so that the vertices that stayed in the subset are more likely, and the vertices that were removed are less likely to be selected on the next iteration. The boosting loop can terminate after a certain number of iterations with no improvement to the list of top independent sets (to allow some flexibility, the algorithm keeps track of several of the top independent sets instead of only storing the best one seen so far).

The procedure can also restart the boosting loop several times with original probe information weights. This feature can be used to prevent convergence to a local optimum, which is possible for high values of the boosting factor.

3. Detailed Explanation of Procedure

The boosting procedure (as a whole) can be viewed as operating on the probability space of all subsets of our graph. Step b.ii.bb provides that the selected subset is independent, so that the probability distribution can only be supported on independent sets (i.e., the distribution is zero on all non-independent sets). In this view, the procedure can converge to a probability distribution where the best independent set has the highest probability. Each iteration of the boosting loop adjusts the probabilities associated with each vertex in the graph. The subset of interest is always drawn randomly according to the current probability distribution.

If the solution S* is known a priori, its selection by the procedure can possibly be guaranteed by initializing the boosting weights in step b.i to be $\forall v \in S^*, w_b(v) \leftarrow 1$, $\forall v \in V-S^*, w_b(v) \leftarrow 0$.

In other words, the associated probability distribution may have a probability of 1 for each vertex v ∈ S*, and a probability of 0 for each remaining vertex v ∈ V−S*.

Given an unlimited time for obtaining a solution (and an appropriate set of parameters), the boosting procedure can converge to this ideal distribution. However, when time is limited, a "good" (i.e., informative) independent set of size ≦M is only "more likely" than other independent sets of similar size. The procedure is provided to give an effective solution in a limited time, and yet be able to improve on it iteratively when more time is permitted (with minimal modifications to the loop terminating conditions).

For example, the best independent set may be, ideally, a fixed point for the algorithm, in the sense that if the procedure starts at a perturbed location in the subset probability space, it should converge to the optimal set. In particular, if the initial probability distribution is heavily favored towards a set that does not differ from the best set in many vertices, the procedure likely converges to the best set.

4. Breaking Edges

In step b.ii.bb of the boosting procedure can keep the vertex that has the higher boosting weight. If vertices have equal boosting weights, one at random (with probability ½) can be selected.

5. Selecting Scaling Factor a

In step b.ii.cc of the boosting algorithm, the weights of those vertices that were selected and kept are boosted (scaled up) by a factor of a≧1, while the weights of discarded vertices are scaled down by the same factor. This has the effect of noting which vertices are selected for membership in the independent set, and increasing the likelihood that these vertices will be selected in the future, with the reverse effect on the discarded vertices. The manner in which the value of the scaling factor a affects the "memory" of the probability space evolution is discussed below. A single "restart" of the procedure (namely, step b.ii) is described.

a) Extreme cases:

a=1: No memory of previous selections. Ignore the current selection, and choose anew on the next iteration. The boosting procedure performs an exhaustive search.

a=∞: Perfect memory. Once a set S of vertices is selected and pruned, and its elements' boosting weights are modified, each of the vertices remaining in the independent set $S_1$ will have a boosting weight of ∞ and each of those thrown out of the independent set due to conflicts will have a boosting weight of 0. Thereafter, the boosting procedure will always choose the independent set selected on the first run.

b) Real values:

The boosting procedure is executed on the same graph model with several values of a ∈ {2, 1.5, 1.2, 1.1}. The executions with higher values of a were observed to terminate a single "restart" after a smaller number of iterations than those with lower values of a. Values of a can be chosen by many methods, known to those with ordinary skill in the art.

6. Choosing M: the Maximum Size of the Independent Set

This section contains a probabilistic analysis of an answer to the following question: What are the bounds on the number of probes, k, that is sufficient to distinguish N known alleles?

In order to answer this question, certain assumptions can be made on the random distribution from which the known alleles are assumed to be drawn.

a) Similar PRV Entries

Assume that each probe, at each index i=1, ... ,N, assumes values 0 and 1 independently and with equal probability. Consider k such probes and two alleles ($HLA_l$ and $HLA_m$). Thus, if $HLA_l$ is fixed:

$HLA_l = (HLA_l[1], \ldots, HLA_l[k])$, then for each j, $Pr(HLA_m[j] = HLA_l[j]) = \frac{1}{2}$ $Pr(HLA_m[j] \neq HLA_l[j]) = \frac{1}{2}$ then, for these two HLA vectors, $$Pr(\text{The Hamming distance between 2 HLA vectors} = x) = \binom{k}{x} 2^{-k}, \quad (11)$$

which can easily be seen as follows:

$$Pr\begin{pmatrix}\text{The Hamming } dist \text{ bet'n} \\ 2 \text{ HLA vectors} = x\end{pmatrix} = Pr\begin{pmatrix}\text{HLA vectors differ in} \\ \text{exactly } x \text{ positions}\end{pmatrix}$$

$$= Pr\begin{pmatrix} x \text{ successes in } k \text{ Bernoulli} \\ \text{trials, where} \\ \text{success} = \{HLA_m[j] \neq HLA_l[j]\} \\ \text{and } p = Pr(\text{success}) = \frac{1}{2} \end{pmatrix}$$

$$= \binom{k}{x}\left(\frac{1}{2}\right)^x\left(\frac{1}{2}\right)^{k-x}$$

$$= \binom{k}{x} 2^{-k}$$

Thus, for a fixed pair of alleles, $$Pr(x \geq 1) = 1 - Pr(x = 0) \quad (12)$$
$$= 1 - \binom{k}{0} 2^{-k} \quad \text{(by (11))}$$
$$= 1 - 2^{-k},$$

and $$Pr(\forall_{pairs} \; x \geq 1) = \prod_{pairs} Pr(x \geq 1) \quad \text{(by indep.)} \quad (13)$$
$$= \prod_{pairs} (1 - 2^{-k})$$
$$= (1 - 2^{-k})^{\#\, pairs} \quad \text{(by (12))}$$
$$= (1 - 2^{-k})^{\binom{N}{2}}$$

since there are N distinct allele vectors and pairs are unordered.

This probability ideally should be greater than $(1-\epsilon)$ for some fixed small $0 < \epsilon \ll 1$, i.e., $$(1 - 2^{-k})^{\binom{N}{2}} \stackrel{want}{>} 1 - \epsilon. \quad (14)$$

First, the left-hand side term is bound:

$$(1 - 2^{-k})^{\binom{N}{2}} = [(1 - 2^{-k})^{2^k}]^{\binom{N}{2} 2^{-k}}$$
$$> \left(e^{-1-2^{-k}}\right)^{\binom{N}{2} 2^{-k}}$$
$$= e^{-\binom{N}{2}(1+2^{-k})2^{-k}}$$

where the inequality comes from the bound (appendix A)

$$\left(1 - \frac{1}{n}\right)^n > e^{-1-\frac{1}{n}} \quad \text{for large } n. \quad (15)$$

For the inequality in (14) to operate, the bound (15) should be in the correct direction. Suppose a>b is desired. If instead a>c is demonstrated and the parameter is selected such that c>b, then it can be concluded from a>c>b that a>b. Therefore, the above inequality chain would work if found (15) holds.

Hereafter, the symbol ⇐ is used to indicate the steps in the inequality reduction that can satisfy the previous statements whenever the parameter in question is selected to satisfy the current statement.

Thus, an inequality (14) can be reduced to the following:

$$e^{-\binom{N}{2}(1+2^{-k})2^{-k}} > 1 - \epsilon \iff -\binom{N}{2}(1+2^{-k})2^{-k} > \ln(1-e) \quad (16)$$

Next, consider the right-hand term: $\ln(1-x) < -x$ for $0 < x < 1$. Again, a>b can be desired. If b<d is demonstrated and the parameter is selected such that a>d, it can be concluded from a>d>b that a>b. This permits the reduction of the inequality (16) to the following:

$$-\binom{N}{2}(1+2^{-k})2^{-k} > -\epsilon \quad (17)$$

$$\iff \epsilon > \binom{N}{2}(1+2^{-k})2^{-k}$$

$$\iff \frac{4^k}{2^k + 1} > (1/\epsilon)\binom{N}{2}, \quad (18)$$

since $$(1 + 2^{-k})2^{-k} = (2^k + 1)2^{-2k} = (2^k + 1)4^{-k}. \quad (19)$$

Furthermore, $$\frac{\beta^2}{\beta+1} = \frac{\beta^2 + \beta - \beta - 1 + 1}{\beta+1} \quad (20)$$

$$= \beta - 1 + \frac{1}{\beta+1} > \beta - 1 \quad \forall \beta > -1.$$

Hence, taking $\beta=2^k$ yields $$\frac{4^k}{2^k+1} > 2^k - 1. \tag{21}$$

Thus, (18) follows if k is chosen to satisfy $$2^k - 1 > (1/\epsilon)\binom{N}{2} \tag{22}$$
$$\iff \boxed{2^k > (1/\epsilon)\binom{N}{2} + 1}$$

The remaining chain of inequalities, from "desired" to "obtained," can now be verified. For example, the inequality (17) can be extended $$-\binom{N}{2}(1+2^{-k})2^{-k} > -\epsilon > \ln(1-\epsilon)$$
$$\implies e^{-\binom{N}{2}(1+2^{-k})2^{-k}} > 1 - \epsilon,$$

which in turn can be extended $$(1-2^{-k})^{\binom{N}{2}} > e^{-\binom{N}{2}(1+2^{-k})2^{-k}} > 1 - \epsilon$$
$$\implies (1-2^{-k})^{\binom{N}{2}} > 1 - \epsilon, \text{ as desired.}$$

Therefore, k (given $\epsilon$, N) is selected to satisfy (22):

$$2^k > (1/\epsilon)\binom{N}{2} + 1$$

A simpler bound on k can be obtained by imposing a stronger condition $$2^k \stackrel{want}{>} (2/\epsilon)\binom{N}{2}, \tag{23}$$

which implies (22) since $$(1/\epsilon)\binom{N}{2} > 1.$$

The right-hand side of equation (23) simplifies to $$(2/\epsilon)\binom{N}{2} = (2/\epsilon)\frac{N(N-1)}{2} = (1/\epsilon)N(N-1),$$

so that $$k > \lg N + \lg(N-1) - \lg \epsilon \tag{24}$$

is equivalent to equation (23). Furthermore, since $2 \lg N > \lg N + \lg(N-1)$, selecting $$k > 2 \lg N - \lg \epsilon$$

certainly gives a value of k that satisfies (23). Therefore, requiring $$\boxed{k > 2 \lg N - \lg \epsilon} \tag{25}$$

imposes the strongest condition of those listed above. Hence, a value of k that satisfies equation (25) also satisfies equation (22), and therefore the original desired inequality (14).

b) Dissimilar PRV Entries. A violation of the similarity assumptions may be modeled by an error term $\delta$. Suppose a probe fails to contribute to a Hamming distance with probability $(1+\delta)/2$. As discussed previously, each position of the HLA code vector can be considered as a Bernoulli trial, where success is defined as the event that $j^{th}$ entry of a code vector contributes to the Hamming distance, i.e., $\{HLA_m[j] \neq HLA_l[j]\}$, so that $$q = Pr(\text{failure}) = (1+\delta)/2$$
$$p = Pr(\text{success}) = (1-\delta)/2$$

Therefore, $$Pr(\text{The Hamm } dist = x) = \binom{k}{x}\left(\frac{1-\delta}{2}\right)^x\left(\frac{1+\delta}{2}\right)^{k-x} \tag{26}$$
$$= \binom{k}{x}(1-\delta)^x(1+\delta)^{k-x}2^{-k}$$

Continuing as before, the following condition can be obtained.

$$Pr(x \geq 1) = 1 - Pr(x = 0) \tag{27}$$
$$= 1 - \binom{k}{0}(1-\delta)^0(1+\delta)^{k-0}2^{-k}$$
$$= 1 - (1+\delta)^k 2^{-k},$$

and $$Pr(\forall_{pairs} x \geq 1) = (1 - (1+\delta)^k 2^{-k})^{\binom{N}{2}}.$$

This probability should be bigger than $(1-\epsilon)$. In other words, $$(1 - (1+\delta)^k 2^{-k})^{\binom{N}{2}} \stackrel{want}{>} 1 - \epsilon \tag{28}$$

$$LHS(28) \stackrel{by\ (15)}{>} e^{-\binom{N}{2}(1+((1+\delta)/2)^k)((1+\delta)/2)^k} \tag{29}$$

$$\impliedby \stackrel{want}{>} 1 - \epsilon$$

$$\iff -\binom{N}{2}\left[1 + \left(\frac{1+\delta}{2}\right)^k\right]\left(\frac{1+\delta}{2}\right)^k > \ln(1-\epsilon) \tag{30}$$

$$\impliedby -\binom{N}{2}\left[1 + \left(\frac{1+\delta}{2}\right)^k\right]\left(\frac{1+\delta}{2}\right)^k \stackrel{want}{>} -\epsilon$$

-continued $$\Leftrightarrow \epsilon > \binom{N}{2}\left[1 + \left(\frac{1+\delta}{2}\right)^k\right]\left(\frac{1+\delta}{2}\right)^k$$

$$\Leftrightarrow \frac{\left(\frac{2}{1+\delta}\right)^{2k}}{\left(\frac{2}{1+\delta}\right)^k + 1} > (1/\epsilon)\binom{N}{2},$$

where the last transformation is obtained as in equation (19), replacing 2 by $2/(1+\delta)$. The same substitution in (21) (i.e., taking $\beta = (2/(1+\delta))^k$ in (20)) yields $$\frac{\left(\frac{2}{1+\delta}\right)^{2k}}{\left(\frac{2}{1+\delta}\right)^k + 1} > \left(\frac{2}{1+\delta}\right)^k - 1 \quad \forall\, k \in \mathbb{N} \tag{31}$$

Thus, equation (30) follows if k is chosen to satisfy $$\left(\frac{2}{1+\delta}\right)^k - 1 > (1/\epsilon)\binom{N}{2} \tag{32}$$

$$\Leftrightarrow \boxed{\left(\frac{2}{1+\delta}\right)^k > (1/\epsilon)\binom{N}{2} + 1}$$

Again, a simpler bound on k can be obtained by imposing a stronger condition $$\left(\frac{2}{1+\delta}\right)^k \stackrel{want}{>} (2/\epsilon)\binom{N}{2} = (1/\epsilon)N(N-1) \tag{33}$$

so that $$lg\left[\left(\frac{2}{1+\delta}\right)^k\right] = k(1 - lg(1+\delta)) \tag{34}$$

$$\stackrel{want}{>} lg\, N + lg(N-1) - lg\,\epsilon$$

$$\Leftarrow k(1 - lg(1+\delta)) > 2\,lg\,N - lg\,\epsilon.$$

$$\boxed{k > \frac{1}{(1 - lg(1+\delta))}[2\,lg\,N - lg\,\epsilon]} \tag{35}$$

c) Non-unit Minimum Hamming Distance. Further, the preferable size k can be estimated for (almost) any desired minimum Hamming distance between allele code vectors. As demonstrated above, the Hamming distance between a pair of HLA vectors is a binomial random variable $x \sim S(n, p)$ where # trials $\equiv n = k$, Pr (success) $\equiv p = (1-\delta)/2$, and Pr (failure) $\equiv q = (1+\delta)/2$:

$$Pr(x) = \binom{k}{x}(1-\delta)^x(1+\delta)^{k-x}2^{-k}$$

Its mean is $np = k(1-\delta)/2$ and variance is $npq = k(1-\delta)/4$. The following estimate can be obtained (using Chernoff bounds):

$$Pr(x \leq k(1-\delta)/4) \leq e^{-k(1-\delta)/16} \tag{36}$$

Chernoff inequality states (see Appendix B for the proof):

$$Pr(S(n,p) \leq (1-\lambda)np) \leq e^{-\frac{\lambda^2}{2}np} \tag{37}$$

$n=k$, $p=(1-\delta)/2$, and let $\lambda = \frac{1}{2}$. Then by equation (37), $$Pr(x \leq k(1-\delta)/4) \leq e^{-\frac{(1-2)^2}{2}k\frac{1-\delta}{2}}$$

$$= e^{-\frac{1}{8}k\frac{1-\delta}{2}}$$

$$= e^{-k(1-\delta)/16}$$

Thus, it can be estimated for which k $$Pr(\forall_{pairs} x \geq k(1-\delta)/4) \geq 1-\epsilon \tag{38}$$

From equation (36), it is possible to obtain $$Pr(x \geq k(1-\delta)/4) \geq 1 - e^{-k(1-\delta)/16}$$

and hence, $$Pr(\forall_{pairs} x \geq k(1-\delta)/4) = Pr(x \geq k(1-\delta)/4)^{\binom{N}{2}} \tag{39}$$

$$\geq (1 - e^{-k(1-\delta)/16})^{\binom{N}{2}}$$

$$\stackrel{want}{>} 1 - \epsilon$$

$\Leftarrow$ (expression (39)) >

$$\exp\left\{-\binom{N}{2}(1 + e^{-k(1-\delta)/16})e^{-k(1-\delta)/16}\right\} \stackrel{want}{>} 1 - \epsilon$$

$$\Leftrightarrow -\binom{N}{2}(1 + e^{-k(1-\delta)/16})e^{-k(1-\delta)/16} > \ln(1-\epsilon)$$

$$\Leftarrow -\binom{N}{2}(1 + e^{-k(1-\delta)/16})e^{-k(1-\delta)/16} > -\epsilon$$

(see (17))

$$\Leftrightarrow \epsilon > \binom{N}{2}(1 + e^{-k(1-\delta)/16})e^{-k(1-\delta)/16}$$

$$\Leftrightarrow \frac{e^{k(1-\delta)/8}}{e^{k(1-\delta)/16}} > (1/\epsilon)\binom{N}{2}$$

$$\Leftarrow e^{k(1-\delta)/16} - 1 > (1/\epsilon)\binom{N}{2} \quad \text{(by (20))}$$

$$\Leftrightarrow e^{k(1-\delta)/16} > (1/\epsilon)\binom{N}{2} + 1$$

$$\Leftarrow e^{k(1-\delta)/16} > (2/\epsilon)\binom{N}{2} = (1/\epsilon)N(N-1)$$

(see (23))

$$\Leftrightarrow k(1-\delta)/16 > \ln N + \ln(N-1) - \ln\epsilon$$

$$\Leftarrow k(1-\delta)/16 > 2\ln N - \ln\epsilon$$

$$\Leftrightarrow k > \frac{16}{1-\delta}[2\ln N - \ln\epsilon]$$

Therefore if, $$k > \frac{16}{1-\delta}[2\ln N - \ln\epsilon] \quad (40)$$

then $$Pr(\forall_{pairs} \; x \geq k(1-\delta)/4) \geq 1-\epsilon$$

For this exemplary probe set (with $k=k(\epsilon, N, \delta)$), an arbitrarily high probability can be obtained, by the selection of $\epsilon$ in (38), that all BLA coding vectors have pairwise Hamming distance of at least $k(1-\delta)/4$. Thus, this exemplary probe set is able to correct $k(1-\delta)/8$ errors by choosing the coding vector closest to that obtained.

The error term $\delta$ should then be estimated. This can be accomplished on a given set S of probes by sampling pairs $\{l, m\}$ of indices on probes from S and examining the resulting 2-vectors on $\{0, 1\}$. The probability of a failure to contribute to the Hamming distance (given by $(1+\delta)/2$) can be estimated by the frequency $f_=$ of observing equal entries in the 2-vector, since each probe with equal entries in the 2-vector fails to contribute to the Hamming distance between alleles l and m. Therefore, $$\delta = 2f_= - 1 \quad (41)$$

Let $f_{\neq}$ denote the frequency of observing unequal entries in the same setting. Thus, $f_= + f_{\neq} = 1$, and it is possible to obtain $$1-\delta = 1-(2f_= - 1) = 2(1-f_=) = 2f_{\neq}. \quad (42)$$

The bound in equation (40) becomes $$k > \frac{16}{2f_{\neq}}[2\ln N - \ln\epsilon] \quad (43)$$
$$= \frac{8}{f_{\neq}}[2\ln N - \ln\epsilon]$$

Thus, to generate distinct coding vectors for all alleles (e.g., to guarantee a Hamming distance $d_H(c_i, c_j) \geq 1$ w.p. $>1-\epsilon$), it is possible to select $M>k$, where k satisfies (35) with $\delta$ estimated as in (41). It is also possible to choose M to allow for error correction of up to $D/2$ errors (guaranteeing w.p. $>(1-\epsilon)$ a minimum Hamming distance $d_H(c_i, c_j) \geq D$): set $$D = k(1-\delta)/4 = kf_{\neq}/2$$

in equation (38), so that $k=2D/f_{\neq}$ should satisfy equation (40), and, again, select $M>k$.

D. Pre-Processing

1. Initial Probe Selection

In section B.2, it was described that starting with all possible probes results in a graph that has many vertices. The discussion below provides certain pre-processing steps that allow the elimination of a large portion of this probe set.

a. Probes that do not hit the BLA region on any allele. Many of the possible length-L probes generally do not provide sequence-specific information about the target. As such, they may be safely left out of our probe selection process. This would allow for a reduction of the starting (perfectly matched) probe set to those probes that are complementary to a subsequence of at least one of the alleles. A way to obtain such set can be as follows. Assume that the allele sequences are provided in the 5' to 3' orientation.

A window of length L can be considered along allele $T_1$. Denote the length of the allelic sequence by $\text{len}(T_1)$, and index elements of the sequence starting with 1, so that the entire allele sequence can be denoted by $T_1[1] \ldots T_1[\text{len}(T_1)]$.

A probe complementary to the allele subsequence seen through the window $[1 \ldots L]$ can be constructed and placed in the set. The window then may be shifted by one nucleotide in the direction of the 3'-end. This process can be repeated until the last window $[k \ldots (L+k-1)]$ reaches the end of the target sequence:

$L+k-1=\text{len}(T_1)$ $k=\text{len}(T_1)-L+1$, thus, generating a set of $(\text{len}(T_1)-L+1)$ probes, each perfectly complementary to $T_1$.

The procedure described above can generate all probes of length L that are, e.g., perfectly complementary to a length-L subsequence of the target (ie., allele) sequence. Depending on the form in which the allele sequences are given, it may also be desirable to include probes corresponding to windows that are partially shifted off the allele, i.e., windows showing a portion of the given allele sequence together with the corresponding 5'-tail of the sequence, if the window is shifted to the left, or the 3'-tail, if the window is shifted to the right. There are $2(L-1)$ such probes, corresponding to indices $[(\text{len}(T_1)-L+2) \ldots (\text{len}(T_1)+1)], \ldots,$ $[\text{len}(T_1) \ldots (\text{len}(T_1)+L-1)]$ for the right-shifted windows and "indices"

$[0 \ldots (L-1)], \ldots, [(2-L) \ldots 1]$ for the left-shifted windows.

This process can be repeated for the other alleles $T_2, \ldots, T_N$. To avoid placing duplicate probes in the set, a generated probe can be added to the set if its sequence is not already present. Alternately, the duplicates can be weeded out subsequently. It should be noted that this may have the added advantage of eliminating probes hitting sequence repeats.

The above-described exemplary process has the effect of eliminating probes that hit genomic sequences outside the target region, including probes that hit introns (if allelic sequences are provided in genomic DNA form) from the original collection of all possible probes of length L. The resulting set may contain only those probes complementary to subsequences of the HLA region, or sub-words of the pool of all allele sequences.

b. Non-informative probes. In the set created as described in the previous section, some (and perhaps many) of the probes would not be able to give any information useful for distinguishing among the alleles. These are the probes that may be drawn from the windows that are shared among the alleles—they hybridize to a common subsequence of the alleles. Any such probe may be useless for discriminating alleles: to such a probe, all alleles will look alike. Therefore, these probes can be safely eliminated from the potential probe set.

To locate all such probes, it is necessary to find the common subsequences of length $\geq L$ of all the alleles, identify the probes complementary to these subsequences, and remove these probes from the set. This can be done as the next step in the "refinement" of the starting probe set, and/or included as a condition in the process for probe addition specified in the previous section.

c. Potential for cross-hybridization. The probes that are likely to hit multiple sites on the target sequence(s), such as those hitting a repeated region, should be eliminated, as is usually done in microarray design, as their use is likely to produce a high level of noise. Each probe is usually expected to have a unique site on the target. See e.g., Lockhart et al., *Nature Biotechnology* 1996, 14:1675; Kaderali and Schliep, An algorithm to select target specific probes for DNA chips at URL http://citeseer.nj.nec.com/kaderali01algorithm.html; Li and Stormo, *Bioinformatics,* 2001, 17:1067.

2. Graph Generation a. Generating Probe Response Vectors. Once a set of initial probes is selected, as described above, a probe response vector (7) must be generated for each of these probes. To do that, given probe j, string-matching is performed on each of the N alleles for the Watson-Crick complement of probe j, and the results are used to set $$v_j[i] = \begin{cases} 1, & \text{if there is a match with allele } T_i \\ 0, & \text{otherwise} \end{cases}$$

b. Choice of Edge Threshold. The edge threshold parameter $\rho$ was used in section B.3 to transform the initial complete edge-weighted graph. Its value determines how many edges remain in the graph, as well as how "independent" each independent set on the graph really is.

- If $\rho$ is too small, there will be very few edges in the graph. Most of the random sets selected by the boosting algorithm will prove to be independent. However, upon examination in post-processing, described in section B.3, it may be found that many of these sets do not possess enough discrimination power to discern all N known alleles.
- If, on the other hand, $\rho$ is too large (e.g., $\rho$>0.5), the graph will be very dense (i.e., have a lot of edges). The algorithm will then have a much harder time finding an independent set of large enough size. The output sets will likely contain much fewer than M vertices, and there may not be enough probes in the candidate sets to discern all N alleles.
- A reasonable value of $\rho$ is obtained by trial and error on a given set of potential probes.

E. Post-Processing

The procedure (as described in section C.1) can return a list of 20 best independent sets, sorted by the total information weight of the constituent vertices. Each set may be composed of e.g., at most M vertices (probes). While the independence and maximum weight conditions can be selected to steer each selected set towards maximum discrimination power, this desired outcome may not be guaranteed. Thus, each of these best independent sets should be checked for redundancy of the allele coding vectors. Given a set S of probe response vectors, the N allele coding vectors generated by S (the rows in (6)) may be extracted and their pairwise Hamming distances $d_H(c_i,c_j)$, $1 \leq i \leq j \leq |S|$ may be computed. If $\min_{\{i,j\}} d_H(c_i, c_j)=0$, the set lacks discrimination power: at least two of the codes are the same, so the set will not be able to discern all known alleles. Such a set should not be used "as is", and should either be discarded or supplemented by additional probes. This may indicate that the set is not truly independent, so the choice of edge threshold $\rho$, discussed in Section D.2.b, was inappropriate.

It is possible to make the testing more stringent, in order to allow for up to D/2 errors in the data, as discussed in Section C.6. Those independent sets of the list of best sets that pass the redundancy testing (by satisfying $\min_{\{i,j\}} d_H(c_i, c_j) \geq D$), in fact satisfy a definition stronger than that formulated for the best independent set. D-best independent set denotes a best independent set with the additional condition $\min_{\{i,j\}} d_H(c_i, c_j) \geq D$.

Those sets that pass the redundancy test can be reordered by aveHamDist=ave$_{\{i,j\}}$ $d_H(c_i,c_j)$: once the minimum allele code separation is guaranteed, the usefulness of a probe set to the HLA typing problem can be judged by the metric aveHamDist.

F. Interpreting Results

Given the best independent set generated by the above-described procedure a determination regarding how it can be converted into a microarray for genotyping or haplotyping experiments must be made.

In order to generate the microarray corresponding to an independent set of vectors yielded by the procedure (followed by post-processing steps from Section E), the DNA sequence for each probe, which was used to generate the probe response vector used in the analysis, should be recalled. The spatial arrangement of these probes on the chip surface can be decided as discussed above in Section A.4.b.

G. Additional Applications

Many extensions of the approaches presented herein are possible within the scope of the present invention. Two exemplary approaches are discussed below.

1. Extending Weight Functions in the Graph Model

The graph model discussed herein relies on the characteristics of the probe response vectors to define the weights of vertices and edges. While this model can generate certain interesting results, it can be extended to a more meaningful model by incorporating the physical properties of the probe sequences and their interactions, some of which are described in Cherepinsky, *Ph.D. Thesis*, New York University 2003, Chapter 3.

In particular, the annotation of all potential probes with physical properties, such as melting temperature, free energy, entropy, and enthalpy of hybridization, for perfect matches and for closest matches in other alleles can be used to define cost functions that determine the weights. While the vertex weight may provide a measure of the performance of the corresponding probe in discriminating among known alleles, the pairwise probe interaction and the resulting competition effects, as described in Cherepinsky, *Ph.D. Thesis*, New York University 2003, Chapter 3, can be reflected in the edge weights.

2. Pooling Real Data from Previously Tested Chips

Another extension of the procedure discussed herein involves the use of data from microarray chips used for HLA typing by different companies. Many biotechnology companies are working on the HLA typing problem in the hope of designing probe sets that give the answer more quickly and with greater accuracy. The sequences of the probes may generally be considered to be proprietary information and thus not shared. As a result, the collection of experimental data from testing the various probes in different combinations and arrangements on the microarray chips generated by different companies may almost never be examined as a whole.

It is possible to employ the probe interaction model presented herein to make use of the aggregate experimental data. Suppose the following information can be obtained: a set of microarray chips along with some identifiers, if not the actual sequences, of the probes comprising each chip, and values measuring the performance of each chip in all previously conducted HLA typing experiments. That is, for each chip, there is a list of unique probe identifiers and some measure of how well this chip performed in HLA typing. It may not be necessary to know the sequence of each probe, so long as the uniqueness of the identifiers can be verified by the company providing the data. It is possible to combine the information from a large number of such previously tested chips to generate a plan for a new microarray chip (i.e., a collection of probe identifiers and their spatial arrangement) with a performance value higher than that of "input" chips by the following process. The probe content and arrangement for each chip, together with its performance value, can be used to build the graph model. Vertex weights can be inferred from chip membership information. Edge weights can be estimated from conditional probabilities using pairwise membership information—that is, by considering two chips at a time, quantities such as the conditional probability that probe $P_i$ was used on chip $C_j$, given that it was used on chip $C_k$, can be estimated. Once the graph is constructed, the boosting-algorithm can be used to generate the best set of probes, as discussed in Section C.1.

All publications cited above are incorporated herein by reference in their entireties.

APPENDIX

Appendix A: Exponential Limit Inequality: Proof

Claim: For large n, $$\left(1 - \frac{1}{n}\right)^n > e^{-1-\frac{1}{n}}. \tag{A1}$$

Proof:

Inequality (A1) is equivalent to $$\ln\left[\left(1 - \frac{1}{n}\right)^n\right] \stackrel{want}{>} -1 - \frac{1}{n}. \tag{A2}$$

Since the series expansion of the logarithm is given by $$\ln(1-x) = -\sum_{j=1}^{\infty} \frac{x^j}{j} = -x - \frac{x^2}{2} - \frac{x^3}{3} - \ldots \text{ for } |x| < 1, \tag{A3}$$

we can expand the left-hand side of (A2) as follows.

$$\ln\left[\left(1 - \frac{1}{n}\right)^n\right] = n\ln\left(1 - \frac{1}{n}\right) \tag{A4}$$

$$= n\left\{-\sum_{j=1}^{\infty} \frac{\left(\frac{1}{n}\right)^j}{j}\right\} \text{ (by (A3))}$$

$$= -n\left\{\sum_{j=1}^{\infty} \frac{1}{jn^j}\right\}$$

$$= -\sum_{j=1}^{\infty} \frac{1}{jn^{j-1}}$$

$$= -1 - \frac{1}{2n} - \frac{1}{3n^2} - \frac{1}{4n^3} - \ldots$$

Thus, inequality (A2) reduces to $$-1 - \frac{1}{2n} - \frac{1}{3n^2} - \frac{1}{4n^3} - \ldots \stackrel{want}{>} -1 - \frac{1}{n} \tag{A5}$$

or, equivalently, $$\iff \frac{1}{3n^2} + \frac{1}{4n^3} + \frac{1}{5n^4} + \ldots \stackrel{want}{<} -\frac{1}{2n} + \frac{1}{n} = \frac{1}{2n} \tag{A6}$$

Now, $$\frac{1}{3n^2} + \frac{1}{4n^3} + \frac{1}{5n^4} + \ldots < \frac{1}{3n^2} + \frac{1}{3n^3} + \frac{1}{3n^4} + \ldots$$

$$= \frac{1}{3n^2}\left(1 + \frac{1}{n} + \frac{1}{n^2} + \ldots\right)$$

$$= \frac{1}{3n^2} \cdot \frac{1}{1 - \frac{1}{n}} \quad \text{(geometric sum)}$$

$$\frac{1}{3n} \cdot \frac{1}{n-1} \stackrel{want}{<} \frac{1}{2n} \quad \text{(by (A6))}$$

Simplifying yields $$\iff \frac{1}{3(n-1)} \stackrel{want}{<} \frac{1}{2}$$

$$\iff 2 < 3(n-1) = 3n - 3$$

$$\iff 5 < 3n,$$

which holds for every $n \geq 2$. Retracing the chain of inequalities, we obtain $$\boxed{\left(1 - \frac{1}{n}\right)^n > e^{-1-\frac{1}{n}} \; \forall \, n \geq 2} \tag{A7}$$

as desired.

Appendix B: Chernoff's Inequality: Proof

Claim:

$$Pr(S(n, p) \leq (1-\epsilon)np) \leq e^{-\frac{\epsilon^2}{2}np}, \epsilon \in (0, 1). \tag{B1}$$

Proof:

S is a Binomial random variable:

$$S(n,p) = X_1 + \ldots + X_n, \tag{B2}$$

where $X_i$ are i.i.d.r.v.'s with $$X_i = \begin{cases} 1 & w.p. \; p \\ 0 & w.p. \; (1-p) \end{cases}, \; i = 1, \ldots, n \tag{B3}$$

Therefore, $$E(S) = \sum_{i=1}^{n} E(X_i) = \sum_{i=1}^{n} p = np. \tag{B4}$$

Since $$S \leq (1-\epsilon)np \quad \text{(B5)}$$
$$\iff S - np \leq -\epsilon np$$
$$\iff \lambda(S - np) \leq -\lambda\epsilon np \quad \forall \lambda > 0$$
$$\iff -\lambda(S - np) \geq \lambda\epsilon np \quad \forall \lambda > 0$$
$$\iff e^{-\lambda(S-np)} \geq e^{\lambda\epsilon np} \quad \forall \lambda > 0,$$

it follows that $$Pr(S \leq (1-\epsilon)np) = Pr(e^{-\lambda(S-np)} \geq e^{\lambda\epsilon np}) \quad \text{(B6)}$$

$$\leq \frac{E[e^{-\lambda(S-np)}]}{e^{\lambda\epsilon np}} \quad \text{(by Markov's inequality)} \quad \text{(B7)}$$

For a proof of Markov's inequality, see, e.g., [24].

From (B2) and (B3), we know that $$S - np = \sum_{i=1}^{n} X_i - np = \sum_{i=1}^{n} (X_i - p). \quad \text{(B8)}$$

Therefore, $$E[e^{-\lambda(S-np)}] = E[e^{-\lambda \sum_i (X_i - p)}] \quad \text{(B9)}$$

$$= E\left[\prod_{i=1}^{n} e^{-\lambda(X_i - p)}\right]$$

$$= \prod_{i=1}^{n} E[e^{-\lambda(X_i - p)}] \quad \text{(by independence)}$$

$$= \{E[e^{-\lambda(X_i - p)}]\}^n \quad \text{(by (B3))}$$

$$E[e^{-\lambda(X_1 - p)}] = pe^{-\lambda(1-p)} + (1-p)e^{-\lambda(-p)} \quad \text{(B10)}$$

$$= e^{\lambda p}(pe^{-\lambda} + (1-p))$$

$$= e^{\lambda p}(1 + \underbrace{p(e^{-\lambda} - 1)}_{u})$$

$$\leq e^{\lambda p}(e^{p(e^{-\lambda} - 1)}) \quad (\text{since } 1 + u \leq e^u \; \forall u)$$

$$= e^{p(e^{-\lambda} - 1 + \lambda)} \quad \text{(B11)}$$

$$\leq e^{p\frac{\lambda^2}{2}},$$

where the last inequality follows from $$e^{-\lambda} \leq 1 - \lambda + \frac{\lambda^2}{2} \quad \forall \lambda > 0 \quad \text{(B12)}$$

$$\implies e^{-\lambda} - 1 + \lambda \leq \frac{\lambda^2}{2}$$

Therefore, by (B9) and (B11), $$E[e^{-\lambda(S-np)}] \leq \left(e^{p\frac{\lambda^2}{2}}\right)^n = e^{\frac{\lambda^2}{2}np} \quad \text{(B13)}$$

and $$Pr(S \leq (1-\epsilon)np) \leq e^{-\lambda\epsilon np} E[e^{-\lambda(S-np)}] \quad \text{(B14)}$$

$$\leq e^{-\lambda\epsilon np} e^{\frac{\lambda^2}{2}np}$$

$$= e^{np\left(\frac{\lambda^2}{2} - \lambda\epsilon\right)} \quad \forall \lambda > 0$$

so that $$f(\lambda^*) = e^{np\left(\frac{\epsilon^2}{2} - \epsilon^2\right)} = e^{-\frac{\epsilon^2}{2}np}$$

and, from (B14), $$\boxed{Pr(S \leq (1-\epsilon)np) \leq e^{-\frac{\epsilon^2}{2}np} \quad \forall \epsilon \in (0, 1)} \quad \text{(B16)}$$

as desired.

It remains to check that the optimizing $\lambda = \lambda^*$ is a minimum of $f(\lambda)$, that is, $f''(\lambda^*) > 0$. By (B15), $$f''(\lambda^*) = f'(\lambda) \cdot np(\lambda - \epsilon) + f(\lambda) \cdot np \,|_{\lambda = \lambda^*}$$

$$= \underbrace{f'(\lambda^*) \cdot np(0)'}_{0} + f(\lambda^*) \cdot np$$

$$= np \, e^{-\frac{\epsilon^2}{2}np} > 0.$$

$\therefore \lambda^* = \epsilon$ is a minimum

What is claimed is:

1. A method for at least one of genotyping or haplotyping a sequence of polymorphic genetic loci in a deoxyribonucleic acid (DNA) sample or identifying a strain variant from the DNA sample, comprising:
   i) providing one or more microarrays that include a set of oligonucleotide probes that are capable of detecting the at least one of the genotypes, the haplotypes or the strain variant;
   ii) hybridizing the DNA sample to the one or more microarrays to create a hybridization pattern;
   iii) determining at least one of a genotype, a haplotype or a strain variant based on the hybridization pattern; and
   iv) optimizing at least one of the set or an arrangement of the oligonucleotide probes as a function of at least one of a match criteria or a mismatch criteria between a true allele contained in the DNA sample and an allele determined by the hybridizing step.

2. The method of claim 1, wherein the one or more microarrays include a set of oligonucleotide probes that are capable of detecting at least one of all known genotypes or all known haplotypes at the polymorphic genetic loci or the strain identification.

3. The method of claim 1, wherein the one or more microarrays are configured to include at least one of an optimal set or an optimal arrangement of oligonucleotide probes.

4. The method of claim 1, wherein the mismatch criteria is the following:

$$\min \sum_{type\ j} w_j E[\prod_{T_j \neq \hat{T}_j}]$$
$$\Leftrightarrow \min \sum_{type\ j} w_j Pr(T_j \neq \hat{T}_j)$$

wherein $T_j$ is a true allele contained in the DNA sample, $\hat{T}_j$ is the allele determined by the hybridization step, $$\prod_X = \begin{cases} 1, & \text{if } X \text{ is true} \\ 0, & \text{otherwise} \end{cases},$$

and $w_j$ is a weight assigned to at least one of the genotype or the haplotype j.

5. The method of claim 4, wherein the weights are provided as follows: $w_j = 1 \forall_j$, wherein $\forall_j$ is a set of at least one of all known genotypes or all known haplotypes at one or more predetermined polymorphic genetic loci.

6. The method of claim 4, wherein the weights are provided as follows: $w_j$ is different for each genotype or haplotype.

7. The method of claim 1, further comprising: at least one of displaying or storing data associated with the at least one of the genotype, the haplotype or the strain variant in a storage arrangement in at least one of a user-accessible format or a user-readable format.

8. A method for at least one of genotyping or haplotyping a sequence of polymorphic genetic loci in a deoxyribonucleic acid (DNA) sample or identifying a strain variant from the DNA sample, comprising:
   i) providing one or more microarrays that include a set of oligonucleotide probes that are capable of detecting the at least one of the genotypes, the haplotypes or the strain variant;
   ii) hybridizing the DNA sample to the one or more microarrays to create a hybridization pattern; and
   iii) determining at least one of a genotype, a haplotype or a strain variant based on the hybridization pattern,
wherein step (iii) produces a vector of n measurements, and wherein n is a number of probes contained on the one or more microarrays.

9. The method of claim 8, wherein the n potential probes provided to identify N known genotypes or haplotypes are each associated with a response vector $\vec{v}_j \in \{0,1\}^N$, $j=1, \ldots, n$.

10. The method of claim 9, further comprising generating a graph G on vertices corresponding to probe response vectors.

11. The method of claim 10, wherein the graph G is a complete edge-weighted and vertex-weighted undirected graph G=(V, E) provided on n vertices, wherein n is the number of potential probes.

12. The method of claim 11, wherein the weights w of each vertex v and each edge e are constrained by: $0 \leq w(v), w(e) \leq 1$.

13. The method of claim 12, wherein the weight w of a vertex v is set to:
   w(v)=min{fraction of 0's, fraction of 1's}.

14. The method of claim 12, wherein the weight w of an edge e={u,v} is set to:
   w(e)=Hamming distance/vector length,
wherein Hamming distance is measured between the probe response vectors corresponding to vertices u and v, and vector length is the length of the probe response vectors, namely, N.

15. The method of claim 11, further comprising modifying the graph G by thresholding the edges such that the modified graph $G_{mod}$ is defined as $G_{mod}=(V, E_{mod})$, wherein $E_{mod}=\{e \in E: w(e) \leq \rho\}$, and $\rho$ is a selected threshold value.

16. The method of claim 15, wherein, for the modified graph $G_{mod}$ and the probe set size M, the following is performed:
   i) initializing a current-best list of independent sets with associated information weights,
   ii) initializing vertex boosting weights to vertex weights w(v),
   iii) defining a probability distribution on the vertex subset based on vertex boosting weights,
   iv) choosing a random subset of vertices of a specified size M based on the probability distribution,
   v) eliminating one of the end-point vertices in each of the edges remaining in the induced subgraph on the random subset,
   vi) modifying the vertex boosting weights by increasing the weights of the vertices that are retained in the subset and decreasing the weights of the vertices that were selected in step (iv) but eliminated in step (v), and
   vii) repeating steps (iii) through (vi) for at least one of a predetermined number of iterations or until no improvement to the list of top independent sets is achieved.

17. The method of claim 16, wherein, for the modified graph $G_{mod}$ and the probe set size M, steps (ii) through (vii) are repeated for a predetermined number of iterations, each iteration starting with reinitializing vertex boosting weights to vertex weights w(v) in step (ii).

18. The method of claim 17, wherein, for a given fixed small $0 < \epsilon \ll 1$, the probe set size M satisfies an inequality $Pr(\forall \text{code pairs, Hamming distance} \geq 1) > 1-\epsilon$.

19. The method of claim 17, wherein, for a given fixed small $0 < \epsilon \ll 1$ and a fixed $\alpha > 1$, the probe set size M satisfies an inequality $Pr(\forall \text{code pairs, Hamming distance} \geq \alpha) > 1-\epsilon$.

20. The method of claim 16, wherein the threshold $\rho$ has a value to enable the graph G to have a sparsity bounded by $A \leq \text{sparsity} \leq B$, wherein the sparsity is definable by the average degree of a vertex in the graph G.

21. The method of claim 20, wherein the lower bound A is a relatively small constant, and the upper bound B is a function of the number of vertices n.

22. The method of claim 8, further comprising: at least one of displaying or storing data associated with at least one of the genotype, the haplotype, the strain variant or the vector in a storage arrangement in at least one of a user-accessible format or a user-readable format.

23. A non-transitory storage medium which includes thereon a software arrangement for providing one or more microarrays, which configures a processing arrangement to perform the procedures comprising:
   i) receiving information regarding a hybridization of the DNA sample to one or more microarrays to create a hybridization pattern, the one or more microarrays including a set of oligonucleotide probes that are capable of detecting at least one set of genotypes or haplotypes for a sequence of polymorphic genetic loci in a deoxyribonucleic acid (DNA) sample or identifying a strain variant from the DNA sample;

ii) determining at least one of a genotype, a haplotype or a strain variant based on the hybridization pattern; and iii) optimizing at least one of the set or an arrangement of the oligonucleotide probes as a function of at least one of a match criteria or a mismatch criteria between a true allele contained in the DNA sample and an allele determined from the hybridization.

24. The storage medium of claim 23, wherein the mismatch criteria is the following:

$$\min \sum_{type\ j} w_j E[\prod_{T_j \neq \hat{T}_j} ]$$
$$\Leftrightarrow \min \sum_{type\ j} w_j Pr(T_j \neq \hat{T}_j)$$

wherein $T_j$ is a true allele contained in the DNA sample, $\hat{T}_j$ is the allele determined by the hybridization step, $$\prod_x = \begin{cases} 1, & \text{if } X \text{ is true} \\ 0, & \text{otherwise} \end{cases},$$

and $w_j$ is a weight assigned to at least one of the genotype or the haplotype j.

25. The storage medium of claim 24, wherein the weights are provided as follows: $w_j=1 \forall_j$, wherein $\forall_j$ is a set of at least one of all known genotypes or all known haplotypes at one or more predetermined polymorphic genetic loci.

26. The storage medium of claim 24, wherein the weights are provided as follows: $w_j$ is different for each genotype or haplotype.

27. A system for at least one of genotyping or haplotyping polymorphic genetic loci or strain identification in a deoxyribonucleic acid (DNA) sample, comprising:
  a processing device which, when executed, is configured to:
  i) receive information regarding a hybridization of the DNA sample to one or more microarrays to create a hybridization pattern, the one or more microarrays including a set of oligonucleotide probes that are capable of detecting at least one set of genotypes or haplotypes for a sequence of polymorphic genetic loci in a deoxyribonucleic acid (DNA) sample or identifying a strain variant from the DNA sample;
  ii) determine at least one of a genotype, a haplotype or a strain variant based on the hybridization pattern; and
  iii) optimize at least one of the set or an arrangement of the oligonucleotide probes as a function of at least one of a match criteria or a mismatch criteria between a true allele contained in the DNA sample and an allele determined by the hybridization.

28. The system of claim 27, wherein the mismatch criteria is the following:

$$\min \sum_{type\ j} w_j E[\Pi_{T_j \neq \hat{T}_j}]$$
$$\Leftrightarrow \min \sum_{type\ j} w_j Pr(T_j \neq \hat{T}_j).$$

wherein $T_j$, is a true allele contained in the DNA sample, $\hat{T}_j$ is the allele determined by the hybridization step, $$\prod_x = \begin{cases} 1, & \text{if } X \text{ is true} \\ 0, & \text{otherwise} \end{cases},$$

and $w_j$ is a weight assigned to at least one of the genotype or the haplotype j.

29. The system of claim 28, wherein the weights are provided as follows:
  $w_j=1 \forall_j$, wherein $\forall_j$ is a set of at least one of all known genotypes or all known haplotypes at one or more predetermined polymorphic genetic loci.

30. The system of claim 28, wherein the weights are provided as follows: $w_j$ is different for each genotype or haplotype.

31. A non-transitory computer-accessible medium having stored thereon computer executable instructions for at least one of genotyping or haplotyping a sequence of polymorphic genetic loci in a deoxyribonucleic acid (DNA) sample or identifying a strain variant from the DNA sample, wherein, when the executable instructions are executed by a processing arrangement, configure the processing arrangement to:
  i) provide one or more microarrays that include a set of oligonucleotide probes that are capable of detecting the at least one of the genotypes, the haplotypes or the strain variant;
  ii) hybridize the DNA sample to the one or more microarrays to create a hybridization pattern; and
  iii) determine at least one of a genotype, a haplotype or a strain variant based on the hybridization pattern,
wherein procedure (iii) produces a vector of n measurements, and wherein n is a number of probes contained on the one or more microarrays.

32. The computer-accessible medium of claim 31, wherein the n potential probes provided to identify N known genotypes or haplotypes are each associated with a response vector $\vec{v}_j \in \{0,1\}^N, j=1, \ldots, n$.

33. The computer-accessible medium of claim 32, further comprising generating a graph G on vertices corresponding to probe response vectors, wherein the graph G is a complete edge-weighted and vertex-weighted undirected graph G=(V, E) provided on n vertices, wherein n is the number of potential probes.

34. The computer-accessible medium of claim 33, wherein the weights w of each vertex v and each edge e are constrained by: $0 \leq w(v), w(e) \leq 1$.

35. The computer-accessible medium of claim 34, wherein at least one of (i) the weight w of a vertex v is set to: w(v)=min{fraction of 0's, fraction of 1's}, or (ii) the weight w of an edge e={u,v} is set to: w(e)=Hamming distance/vector length, wherein the Hamming distance is measured between the probe response vectors corresponding to vertices u and v, and wherein the vector length is the length of the probe response vectors N.

36. The computer-accessible medium of claim 33, further comprising modifying the graph G by thresholding the edges such that the modified graph $G_{mod}$ is defined as $G_{mod}$=(V, $E_{mod}$), wherein $E_{mod}$={e ∈ E: w(e)≤ρ}, and ρ is a selected threshold value.

37. The computer-accessible medium of claim 36, wherein, for the modified graph $G_{mod}$ and the probe set size M, when the executable instructions are executed, the processing arrangement is further configured to:
  iv) initialize a current-best list of independent sets with associated information weights, v) initialize vertex boosting weights to vertex weights w(v),
vi) defining a probability distribution on the vertex subset based on vertex boosting weights,
vii) choose a random subset of vertices of a specified size M based on the probability distribution,
viii) eliminate one of the end-point vertices in each of the edges remaining in the induced subgraph on the random subset,
ix) modify the vertex boosting weights by increasing the weights of the vertices that are retained in the subset and decreasing the weights of the vertices that were selected in procedure (vii) but eliminated in procedure (viii), and
x) repeat procedures (vi) through (ix) for at least one of a predetermined number of iterations or until no improvement to the list of top independent sets is achieved.

38. The computer-accessible medium of claim 37, wherein, for the modified graph $G_{mod}$ and the probe set size M, when executed, the processing arrangement is further configured to repeat procedures (v) through (x) for a predetermined number of iterations, and to start each iteration with a reinitialization of the vertex boosting weights to the vertex weights w(v) in procedure (v).

39. The computer-accessible medium of claim 38, wherein at least one of (i) for a given fixed small $0<\epsilon<<1$, the probe set size M satisfies an inequality $Pr(\forall \text{code pairs, Hamming distance} \geq 1)>1-\epsilon$, or (ii) for a given fixed small $0<\epsilon<<1$ and a fixed $\alpha>1$, the probe set size M satisfies an inequality $Pr(\forall \text{code pairs, Hamming distance} \geq \alpha)>1-\epsilon$.

40. The computer-accessible medium of claim 37, wherein the threshold p has a value to enable the graph G to have a sparsity bounded by $A \leq \text{sparsity} \leq B$, wherein the sparsity is definable by the average degree of a vertex in the graph G, wherein the lower bound A is a relatively small constant, and wherein the upper bound B is a function of the number of vertices n.

41. A system for at least one of genotyping or haplotyping a sequence of polymorphic genetic loci in a deoxyribonucleic acid (DNA) sample or identifying a strain variant from the DNA sample, comprising:
a processing device that, when executed, is configured to:
i) provide one or more microarrays that include a set of oligonucleotide probes that are capable of detecting the at least one of the genotypes, the haplotypes or the strain variant;
ii) hybridize the DNA sample to the one or more microarrays to create a hybridization pattern; and
iii) determine at least one of a genotype, a haplotype or a strain variant based on the hybridization pattern,
wherein procedure (iii) produces a vector of n measurements, and wherein n is a number of probes contained on the one or more microarrays.

42. The system of claim 41, wherein the n potential probes provided to identify N known genotypes or haplotypes are each associated with a response vector $\vec{v}_j \in \{0,1\}^N, j=1,\ldots,n$.

43. The system of claim 42, further comprising generating a graph G on vertices corresponding to probe response vectors, wherein the graph G is a complete edge-weighted and vertex-weighted undirected graph G=(V, E) provided on n vertices, wherein n is the number of potential probes.

44. The system of claim 43, wherein the weights w of each vertex v and each edge e are constrained by: $0 \leq w(v)$, $w(e) \leq 1$.

45. The system of claim 44, wherein at least one of (i) the weight w of a vertex v is set to: w(v)=min{fraction of 0's, fraction of 1's}, or (ii) the weight w of an edge e={u,v} is set to: w(e)=Hamming distance/vector length, wherein the Hamming distance is measured between the probe response vectors corresponding to vertices u and v, and wherein the vector length is the length of the probe response vectors N.

46. The system of claim 43, further comprising modifying the graph G by thresholding the edges such that the modified graph $G_{mod}$ is defined as $G_{mod}=(V, E_{mod})$, wherein $E_{mod}=\{e \in E: w(e) \leq \rho\}$, and $\rho$ is a selected threshold value.

47. The system of claim 46, wherein, for the modified graph $G_{mod}$ and the probe set size M, when executed, the processing device is further configured to:
iv) initialize a current-best list of independent sets with associated information weights,
v) initialize vertex boosting weights to vertex weights w(v),
vi) define a probability distribution on the vertex subset based on vertex boosting weights,
vii) choose a random subset of vertices of a specified size M based on the probability distribution,
viii) eliminate one of the end-point vertices in each of the edges remaining in the induced subgraph on the random subset,
ix) modify the vertex boosting weights by increasing the weights of the vertices that are retained in the subset and decreasing the weights of the vertices that were selected in procedure (vii) but eliminated in procedure (viii), and
x) repeat procedures (vi) through (ix) for at least one of a predetermined number of iterations or until no improvement to the list of top independent sets is achieved.

48. The system of claim 47, wherein, for the modified graph $G_{mod}$ and the probe set size M, when executed, the processing device is further configured to repeat procedures (v) through (x) for a predetermined number of iterations, and to start each iteration with a reinitialization of the vertex boosting weights to the vertex weights w(v) in procedure (v).

49. The computer-accessible medium of claim 48, wherein at least one of (i) for a given fixed small $0<\epsilon<<1$, the probe set size M satisfies an inequality $Pr(\forall \text{code pairs, Hamming distance} \geq 1)>1-\epsilon$, or (ii) for a given fixed small $0<\epsilon<<1$ and a fixed $\alpha>1$, the probe set size M satisfies an inequality $Pr(\forall \text{code pairs, Hamming distance} \geq \alpha)>1-\epsilon$.

50. The computer-accessible medium of claim 47, wherein the threshold p has a value to enable the graph G to have a sparsity bounded by $A \leq \text{sparsity} \leq B$, wherein the sparsity is definable by the average degree of a vertex in the graph G, wherein the lower bound A is a relatively small constant, and wherein the upper bound B is a function of the number of vertices n.

* * * * *